(12) United States Patent
Rodriguez Oquendo

(10) Patent No.: US 10,265,379 B2
(45) Date of Patent: Apr. 23, 2019

(54) USE OF RECOMBINANT LYMPHOCYTE ACTIVATION GENE-3 AS A COMPANION THERAPEUTIC FOR PATIENTS AT RISK FOR CARDIOVASCULAR DISEASE AND OTHER CHRONIC INFLAMMATORY DISEASES

(71) Applicant: Annabelle Rodriguez Oquendo, Farmington, CT (US)

(72) Inventor: Annabelle Rodriguez Oquendo, Farmington, CT (US)

( * ) Notice: Subject to any disclaimer, the term of this patent is extended or adjusted under 35 U.S.C. 154(b) by 0 days.

(21) Appl. No.: 15/262,618

(22) Filed: Sep. 12, 2016

(65) Prior Publication Data

US 2017/0312338 A1 Nov. 2, 2017

Related U.S. Application Data

(60) Provisional application No. 62/219,429, filed on Sep. 16, 2015.

(51) Int. Cl.
*A61K 38/17* (2006.01)
*A61K 31/10* (2006.01)
*A61K 45/06* (2006.01)
*C12Q 1/6883* (2018.01)
*G01N 33/68* (2006.01)

(52) U.S. Cl.
CPC .......... *A61K 38/1774* (2013.01); *A61K 31/10* (2013.01); *A61K 45/06* (2013.01); *C12Q 1/6883* (2013.01); *G01N 33/6872* (2013.01); *C12Q 2600/156* (2013.01); *G01N 2333/70503* (2013.01); *G01N 2800/32* (2013.01)

(58) Field of Classification Search
None
See application file for complete search history.

(56) References Cited

U.S. PATENT DOCUMENTS

| | | | |
|---|---|---|---|
| 6,410,509 | B1 | 6/2002 | Triebel |
| 2011/0008331 | A1* | 1/2011 | Triebel ............... A61K 38/1774 424/133.1 |

OTHER PUBLICATIONS

Joana Viola & Oliver Soehnlein—Atherosclerosis—a matter of unresolved inflammation. Semin Immunol, 2015, vol. 27, pp. 184-193.
Executive Summary. Third Report of the National Cholesterol Education Program (NCEP) Expert Panel on Detection, Evaluation, and Treatment of High Blood Cholesterol in Adults. s.I.: NIH Publication No. 01-3670, 2001.
Sekar Kathiresan & Deepak Srivastava—Genetics of human cardiovascular disease. Cell, 2012, vol. 148, pp. 1242-1257.
Huard B, Tournier M, Hercend T, Triebel F, Faure F.—Lymphocyte-activation gene 3/major histocompatibility complex class II interaction modulates the antigenic response of CD4+ T lymphocytes. Eur J Immunol, 1994, vol. 24, pp. 3216-3221.
Triebel, F.—LAG-3: a regulator of T-cell and DC responses and its use in therapeutic vaccination. TRENDS Immunol, 2003, vol. 24, pp. 619-622.
Workman CJ, Wang Y, EL Kasmi KC, Pardoll DM, Murray PJ, Drake CG, Vignali DA.—LAG-3 regulates plasmacytoid dendritic cell homeostasis. J Immunol, 2009, vol. 182, pp. 1885-1891.
Workman CJ, Vignali DA—The CD4-related molecule, LAG-3 (CD223), regulates the expansion of activated T cells. Eur J Immunol, 2003, vol. 33, pp. 970-979.
Li N, Wang Y, Forbes K, Vignali KM, Heale BS, Saftiq P, Hartmann D, Black RA, Rossi JJ, Blobel CP, Dempsey PJ, Workman CJ, Vignali DA.—Metalloproteases regulate T-cell proliferation and effector function via LAG-3. EMBO, 2007, vol. 26, pp. 494-504.
Sierro S, Romero P, Speiser DE—The CD4-like molecule LAG-3, biology and therapeutic applications. Expert Opin Ther Targets 2011; 15:91-101.
Golden et al., Arteriosclerosis, Thrombosis, and Vascular Biology, 34: A359 (2014).
Lienhardt et al, Active tuberculosis in Africa is associated with reduced Th1 and increased Th2 activity in vivo, G. s. I. : Eur J Immunol, 2002, vol. 32, pp. 1605-1613.
Triebel et al.—A soluble lymphocyte activation gene-2 (sLAG-3) protein as a prognostic factor in human breast cancer expressing estrogen or progesterone receptors. M-F. s.I.: Cancer Letters, 2006, vol. 235, pp. 147-153.
Kisielow M, Kisielow J, Capoferri-Sollami G, Karjalainen K—Expression of lymphocyte activation gene 3 (LAG-3) on B cells is induced by T cells. Eur J Immunol 2005; 35:2081-2088.
Baixeras E, Huard B, Miossec C, Jitsukawa S, Martin M, Hercend T, Auffray C, Triebel F, Piatier-Tonneau D.—Characterization of the lymphocyte activation gene 3-encoded protein. A new ligand for human leukocyte antigen class II antigens. J Exp Med 1992;176:327-337.

(Continued)

*Primary Examiner* — Zachary S Skelding
(74) *Attorney, Agent, or Firm* — Royal W. Craig; Gordon Feinblatt LLC

(57) ABSTRACT

A method for classifying patients at risk for cardiovascular disease, other chronic inflammatory diseases, cardiovascular and/or non-cardiovascular morbidity and mortality based on a risk assessment for lymphocyte activation gene 3 (LAG3) protein deficiency, and for mediating the risk using recombinant lymphocyte activation gene-3 or LAG3 mimetic as a companion therapeutic alone or in combination with a statin and/or an anti-hyperlipidemic drug. The risk assessment is two-prong, beginning with a qualitative determination whether a subject has or is predisposed to abnormal expression of inflammasomes, heightened risk for inflammation and/or to dysfunctional HDL, followed by a quantitative assay or genetic screen for a polymorphism that occurs in the coding sequence of the LAG3 gene. Given positive indication, recombinant LAG3 and/or LAG3 mimetic is used alone or in combination with the therapeutic use of a cholesterol mediating drug for treatment.

33 Claims, 21 Drawing Sheets
(4 of 21 Drawing Sheet(s) Filed in Color)
Specification includes a Sequence Listing.

(56) References Cited

OTHER PUBLICATIONS

Morales O, Mrizak D, Francois V, Mustapha R, Miroux C, Depil S, Decouvelaere AV, Lionne-Huyghe P, Auriault C, De Launoit Y, Pancre V, Delhem N.—Epstein-Barr virus infection induces an increase of T regulatory type 1 cells in Hodgkin lymphoma patients. Br J Haematol Jul. 9, 2014. Epub ahead of print.

Lichtman AH, Binder CJ, Tsimikas S, Witztum JL—Adaptive immunity in atherogenesis: new insights and therapeutic approaches. J Clin Invest, 2013, vol. 123, pp. 27-36.

Woo S-R, Li N, Bruno TC, Forbes K, Brown S, Workman C, Drake CG, Vignali DAA.—Differential subcellular localization of the regulatory T-cell protein LAG-3 and the coreceptor CD4. Eur J Immunol 2010;40:1768-1777.

Simons K, Toomre D.—Lipid rafts and signal transduction. Nat Rev Mol Cell Biol 2000; 1:31-39.

Schamel WW, Reth M.—Monomeric and oligomeric complexes of the B cell antigen receptor. Immunity. 2000;13:5-14.

Takata M, Sabe H, Hata A, Inazu T, Homma Y, Nukada T, Yamamura H, Kurosaki T.—Tyrosine kinases Lyn and Syk regulate B cell receptor-coupled Ca2+ mobilization through distinct pathways. EMBO J. 1994; 13:1341-9.

Blix ES, Irish JM, Husebekk A, Delabie J, Forfang L, Tierens AM, Myklebust JH, Kolstad A.—Phospho-specific flow cytometry identifies aberrant signaling in indolent B-cell lymphoma. BMC Cancer 2012;12:478.

Coggeshall KM, McHugh JC, Altman A.—Predominant expression and activation-induced tyrosine phosphorylation of phospholipase C-gamma 2 in B lymphocytes. Proc Natl Acad Sci U S A. 1992; 89:5660-4.

Sugawara H, Kurosaki M, Takata M, Kurosaki T.—Genetic evidence for involvement of type 1, type 2 and type 3 inositol 1,4,5-trisphosphate receptors in signal transduction through the B-cell antigen receptor. EMBO J. 1997;16:3078-88.

Hyka N, Dayer J-M, Modoux C, Kohno T, Edwards III CK, Roux-Lombard P, Burger D.—Apolipoprotein A-I inhibits the production of interleukin-1β and tumor necrosis factor-α by blocking contact-mediated activation of monocytes by T lymphocytes. Blood 2001; 97:2381-2389.

Manichaikul et al—Arterioscler Thromb Vasc Biol. 2012; 32:1991-1999.

Garlanda C, Dinarello CA, Mantovani A.—The interleukin-1 family: back to the future. Immunity, 2013, vol. 39, pp. 1003-1018.

Sierro et al.—"The CD4-like molecule LAG-3, biology and therapeutic applications", Section 3.

Andreae et al.—Maturation and activation of dendritic cells induced by lymphocyte activation gene-3 (CD223), J Immunol, 168:3874-80 (2002).

* cited by examiner

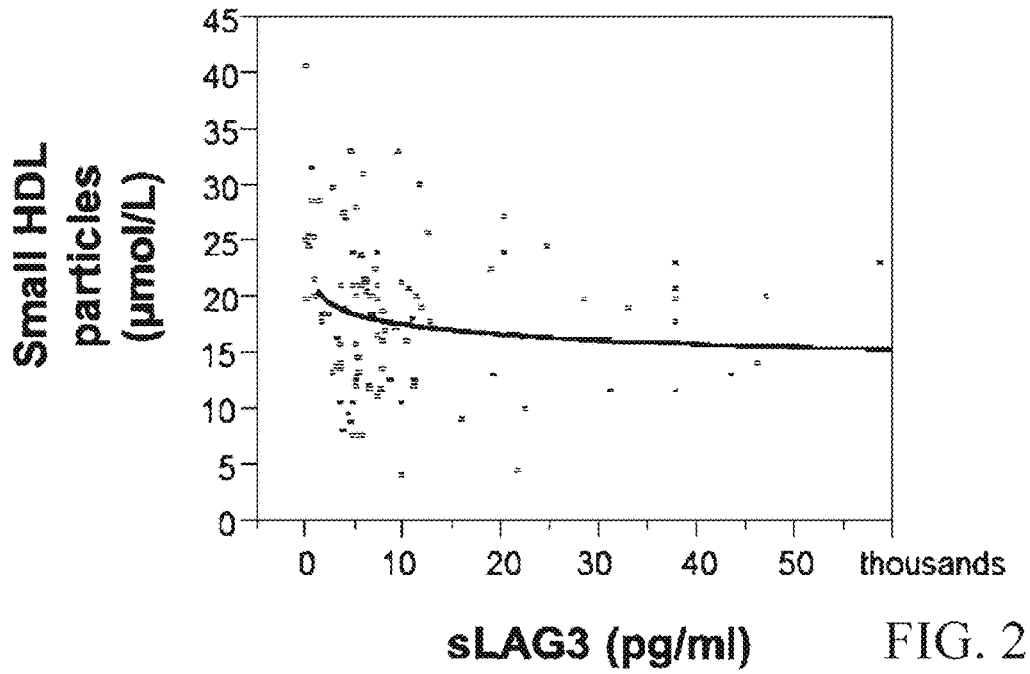

FIG. 2

Murine soluble Lag-3, extracellular, without signal peptide. Accession Number: UniProtKB-Q61790

SGPGKELFVVWAQEGAPVHLPCSLKSPNLDPNFLRRGGVIWQHQPDSGQPTPIPALDLHQ
GMPSPRQPAPGRYTVLSVAPGGILRSGRQPLHPHVQLEERGLQRGDFSLWLRPALRTDAGE
YHATVRLPNRALSCSLRLRVGQASMIASPSGVLKLSDWVLLNCSFSRPDRPVSVHWFQGQ
NRVPVYNSPRHFLAETFLLLPQVSPLDSGTWGCVLTYRDGFNVSITYNLKVGLEPVAPL
TVYAAEGSRVELPCHLPPGVGTPSLLIAKWTPPGGGPELPVAGKSGNFTLHLEAVGLAQA
GTYTCSIHLQGQQLNATVTLAVITVTPKSFGLPGSRGKLLCEVTPASGKERFVWRPLNNL
SRSCPGPVLEIQEARLLAERWQCQLYEGQRLLGATVYAAESSSGAHSARRISGDLKGGHL

Human LAG-3 proteins. Accession number: NP_002277, 525 amino acids full length mweaqflgll flqplwvapv kplqpgaevp vvwaqegapa qlpcsptipl qdlsllrrag
vtwqhqpdsg ppaaapghpl apgphpaaps swgprprryt vlsvgpgglr sgrlplqprv
qldergrqrg dfslwlrpar radageyraa vhlrdralsc rlrlrlgqas mtasppgslr
asdwvilncs ferpdrpasv hwfrnrgqgr vpvresphhh laesflflpq vspmdsgpwg
ciltyrdgfn vsimynltvl glepptpltv yagagarvgl pcrlpagvgt rsfltakwtp
pgggpdllvt qdngdftlrl edvsqaqagt ytchihlqeq qlnatvtlai itvtpksfgs
pgslgkllce vtpvsgqerf vwsaldtpsq rsfsgpwlea qeaqllsqpw qcqlyqgerl
lgaavyftel sspgaqrsgr apqalpaghl llflilgvls lllvtgafg fhlwrrqwrp
rrfsalaqgi hppqaqskie eleqepepep spepepepep epeql

FIG. 4

Human LAG-3 proteins. Accession number: XXX, truncated soluble LAG-3

Table 2. Multivariable regression analysis of independent predictors for plasma LAG-3 (A) and HDL-C (B): MESA.

A. Multivariable regression analysis of independent predictors for plasma LAG-3: MESA.

| Covariates | N | Beta | SE | P value |
|---|---|---|---|---|
|  | 5137 |  |  |  |
| Rs10846744: |  |  |  |  |
| GG: |  | 183.98 | 91.1 | 0.04 |
| GC: |  | -261.8 | 80.1 | 0.001 |
| Race: |  |  |  | 0.0005 |
| White |  | -641.37 | 408.5 |  |
| Chinese |  | 491.2 | 1061.6 |  |
| African American |  | 862.7 | 450.2 |  |
| Age |  | -19.81 | 6.7 | 0.003 |
| Lipid meds |  | 153.22 | 70.5 | 0.03 |
| Smoking |  | -10.95 | 2.72 | <0.0001 |

Covariates included race, PCs of ancestry, age, study sites, sex, HgbA1c, BMI, lipid medications, lipids (TC, LDL-C, HDL-C), smoking pack years, systolic BP, and diastolic BP. LAG3 was log-transformed.

B. Multivariable regression analysis of independent predictors for HDL-C: MESA.

| Covariates | N | Beta | SE | P value |
|---|---|---|---|---|
|  | 4953 |  |  |  |
| LAG3 |  | -0.770 | 0.28 | 0.007 |
| Age |  | 0.056 | 0.02 | 0.006 |
| Triglycerides |  | -0.062 | 0.002 | <0.0001 |
| Sex: Men |  | 5.67 | 0.19 | <0.0001 |
| BMI |  | -0.623 | 0.035 | <0.0001 |
| HgbA1c |  | -0.450 | 0.181 | 0.01 |
| Alcohol |  | 3.28 | 0.370 | <0.0001 |
| Systolic BP |  | 0.027 | 0.01 | 0.03 |

Covariates included race, PCs of ancestry, age, study sites, sex, HgbA1c, BMI, lipid medications, lipids (triglycerides), smoking pack years, current alcohol use, systolic BP, and diastolic BP. LAG3 was log-transformed.

FIG. 5

Table 3. Association of plasma LAG3 with CHD in MESA participants.

| Variable | Odds Ratio | 95% CI |
|---|---|---|
| **LAG3 (log scale) | 1.15 | 1.02-1.28 |
| *Age | 2.41 | 1.81-3.21 |
| *Sex | 2.10 | 1.50-2.94 |
| †Systolic blood pressure | 1.60 | 1.25-2.06 |
| **LDL cholesterol | 1.79 | 1.11-2.87 |
| ††Total cholesterol | 0.60 | 0.37-0.97 |
| #Lipid medication | 1.60 | 1.18-2.17 |
| **HgbA1c | 1.09 | 1.01-1.14 |
| #Smoking pack-years | 1.07 | 1.00-1.14 |

Table 4. Association of plasma LAG3 with CHD in MESA participants with HDL-C ≥ 60 mg/dL.

| Variable | Odds Ratio | 95% CI |
|---|---|---|
| *LAG3 (log scale) | 1.45 | 1.12-1.85 |
| **Age | 2.79 | 1.35-5.78 |
| *Sex | 3.80 | 1.68-8.56 |
| **Diastolic blood pressure | 0.49 | 0.26-0.92 |

Table 5. Plasma LAG3 as a CHD risk predictor compared with Framingham risk score.

| | Beta | SE | P-value |
|---|---|---|---|
| Model 1: (N=5468) | | | |
| Framingham risk score (log scale) | 0.872 | 0.093 | <0.0001 |
| Model 2: (N=5468) | | | |
| Framingham risk score (log scale) | 0.875 | 0.094 | <0.0001 |
| LAG3 (log scale) | -0.065 | 0.031 | 0.039 |
| Model 3: (N=5468) | | | |
| Framingham risk score (log scale) | 0.891 | 0.095 | <0.0001 |
| Model 4: (N=5468) | | | |
| Framingham risk score (log scale) | 0.893 | 0.095 | <0.0001 |
| LAG3 (log scale) | -0.064 | 0.031 | 0.044 |

Table 6. Association of plasma LAG3 with inflammatory markers in MESA participants.

| Outcomes | N | Beta | SE | P-value |
|---|---|---|---|---|
| IL-2 | 2386 | -0.002 | 0.004 | 0.624 |
| IL-6 | 5414 | -0.006 | 0.044 | 0.203 |
| IL-10 | 2350 | 0.035 | 0.007 | <0.0001 |
| CD40 ligand | 851 | -0.0004 | 0.010 | 0.966 |
| sTNFαR | 2396 | -0.001 | 0.003 | 0.824 |
| hs-CRP | 5533 | -0.013 | 0.007 | 0.087 |

FIG. 12

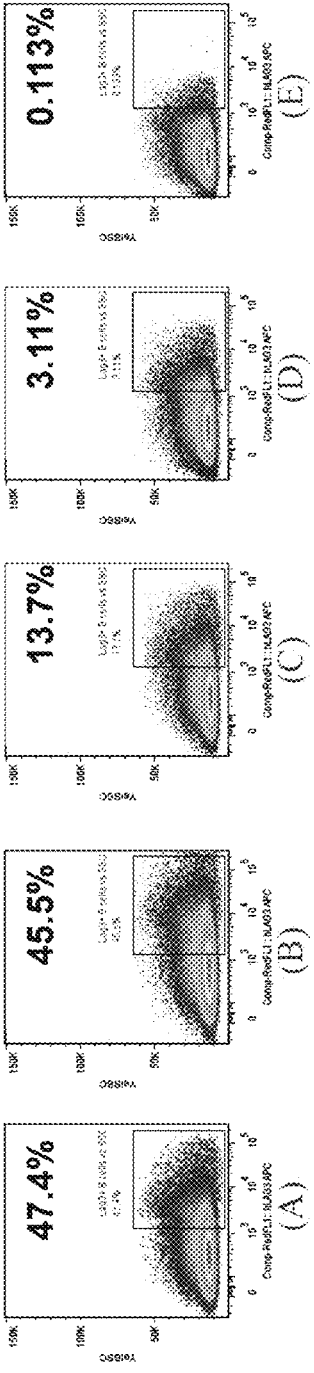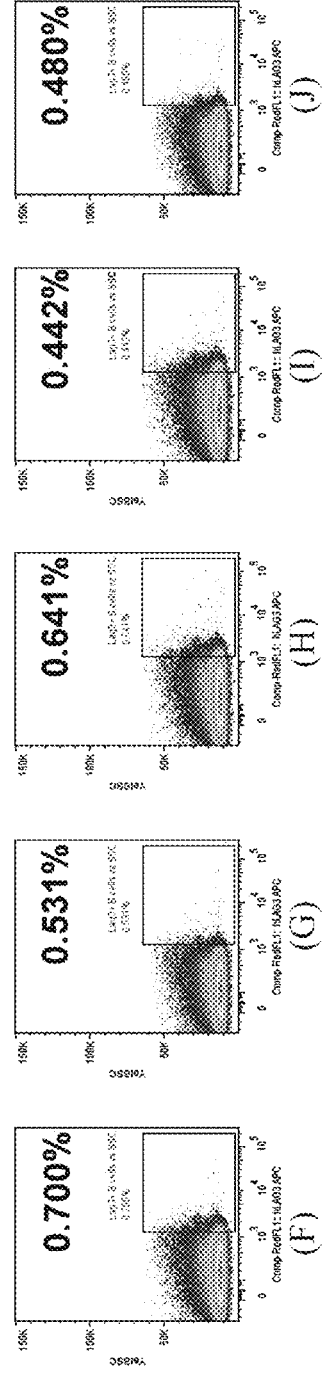
FIG. 16 Wild-type mouse B splenocytes (approximately 1 million) were incubated with varying concentrations of recombinant human LAG3 (μg protein/ml) and then stained with anti-human LAG3 (upper panels, 5 μl per condition) or control mouse IgG1 antibodies and then analyzed by flow cytometry.

Wild-type mouse B splenocytes (approximately 1 million) were incubated with varying concentrations of LG1003 (μg protein/injection) and then stained with anti-human LAG3 (upper panels, 2 ul per test) or control mouse IgG1 antibodies and then analyzed by flow cytometry.

USE OF RECOMBINANT LYMPHOCYTE ACTIVATION GENE-3 AS A COMPANION THERAPEUTIC FOR PATIENTS AT RISK FOR CARDIOVASCULAR DISEASE AND OTHER CHRONIC INFLAMMATORY DISEASES

CROSS-REFERENCE TO RELATED APPLICATION

This application derives priority from U.S. Provisional Patent Application Ser. No. 62/219,429 filed 16 Sep. 2015.

REFERENCE TO AN ELECTRONIC SEQUENCE LISTING

The contents of the electronic sequence listing (Lag 3_Revised_064917_v2txt; Size: 19KB; and Date of Creation: Jun. 19, 2017) is herein incorporated by reference in its entirety.

BACKGROUND OF THE INVENTION

1. Field of the Invention

The present invention relates to disease detection and treatment for diseases such as cardiovascular and immune diseases and, more specifically, to a method for classifying patients at risk for cardiovascular disease, other chronic inflammatory diseases, and cardiovascular and non-cardiovascular mortality based on a risk assessment for lymphocyte activation gene 3 (LAG3) protein deficiency, and for mediating the risk using recombinant lymphocyte activation gene-3 as a companion therapeutic.

2. Description of the Background

It is now well-established that atherosclerosis is a chronic inflammatory disease, with coronary artery vessels infiltrated by innate and adaptive immune cells and cholesterol plaque that ultimately leads to vessel occlusion and clinical disease [Atherosclerosis—a matter of unresolved inflammation. Viola J, Soehnlein O. s.l.: Semin Immunol, 2015, Vol. 27, pp. 184-193]. A number of cardiovascular disease (CVD) risk factors are used clinically to assess atherosclerotic risk in patients, including hypertension, diabetes mellitus, lipids, age, and sex [Executive Summary. Third Report of the National Cholesterol Education Program (NCEP) Expert Panel on Detection, Evaluation, and Treatment of High Blood Cholesterol in Adults. s.l.: NIH Publication No. 01-3670, 2001]. In this era of precision medicine, it is understood that genetic causes also exert major influences on CVD risk. There are now a number of genome wide association studies (GWAS) that have identified known and novel loci that are significantly associated with CVD, especially diseases such as atherosclerosis and myocardial infarction [Genetics of human cardiovascular disease. Kathiresan S. Srivastava D. s.l.: Cell, 2012, Vol. 148, pp. 1242-1257].

It has been shown that the rs10846744 single nucleotide polymorphism (SNP) within the SR-B1 gene, SCARB1 (located on chromosome 12:q24.31), is significantly associated with subclinical atherosclerosis and CVD. In issued U.S. Pat. No. 9,334,538, the present inventor disclosed a method of genotyping women in order to identify the presence of the rs10846744 mutation of the SCARB1 gene (located on chromosome 12:q24.31). This was significantly associated with subclinical atherosclerosis (SCA) and incident cardiovascular disease (CVD) in participants of the Multi-Ethnic Study of Atherosclerosis (MESA). Specifically, carriers of the risk C allele had significantly increased odds for incident CVD, and in a multivariable regression model this relationship was not attenuated by inclusion of traditional CVD risk factors such as age, body mass index, hypertension, smoking, renal disease, statin use or lipid levels (whether total cholesterol, LDL-cholesterol [LDL-C], HDL-C, or triglycerides). These findings strongly suggested that other factors or pathways might be causal in the association of this genetic variant with incident CVD.

Interestingly, rs10846744 resides within the first intron of SCARB1 and bioinformatic analysis revealed that this SNP resides within a regulatory region. The data suggested that this SNP could transcriptionally regulate genes on the same chromosome (intra-chromosomal) or inter-chromosomally. The present inventor investigated this possibility and a number of transcriptionally regulated gene candidates emerged. One in particular, lymphocyte activation gene-3 (LAG-3) is also located on chromosome 12 and was investigated further. LAG3 is a significant regulator in T lymphocyte activation [Lymphocyte-activation gene 3/major histocompatibility complex class II interaction modulates the antigenic response of CD4+ T lymphocytes. Huard B, Tournier M, Hercend T, Triebel F, Faure F. s.l.: Eur J Immunol, 1994, Vol. 24, pp. 3216-3221]. LAG3 belongs to the Ig superfamily and is a ligand to MHC class II molecules of antigen-presenting cells [LAG-3: a regulator of T-cell and DC responses and its use in therapeutic vaccination. F., Triebel. s.l.: TRENDS Immunol, 2003, Vol. 24, pp. 619-622]. It is expressed in B cells, T cells, and NK lymphocytes, monocytes, and dendritic cells (DC) and its major function is thought to be a negative regulator of activated T cells by controlling effector T cell expansion and homeostasis [LAG-3 regulates plasmacytoid dendritic cell homeostasis. Workman C J, Wang Y, El Kasmi K C, Pardoll D M, Murray P J, Drake C G, Vignali D A. s.l.: J Immunol, 2009, Vol. 182, pp. 1885-1891; The CD4-related molecule, LAG-3 (CD223), regulates the expansion of activated T cells. Workman C J, Vignali D A. s.l.: Eur J Immunol, 2003, Vol. 33, pp. 970-979]. Cell surface LAG3 is subject to cleavage by ADAM10 and ADAM17 metalloproteases, which results in soluble LAG3 (sLAG3) [Metalloproteases regulate T-cell proliferation and effector function via LAG-3. Li N, Wang Y, Forbes K, Vignali K M, Heale B S, Saftiq P, Hartmann D, Black R A, Rossi J J, Blobel C P, Dempsey P J, Workman C J, Vignali D A. s.l.: EMBO, 2007, Vol. 26, pp. 494-504].

In vitro and ex vivo approaches were taken to examine the association of rs10846744 with LAG3 in biospecimens isolated from hyperalphalipoproteinemic (HALP) subjects. It was found that rs10846744 is significantly associated with alterations in the expression and function of LAG3, and markers of intracellular inflammasomes such as NLRP3.

LAG3 is located near the CD4 loci on chromosome 12 (chr 12:p13) while rs10846744 is located on chr12:q24.32. LAG3 has a similar function, if not a competitive one against CD4, by binding MHC class II on antigen-presenting cells. [Sierro S, Romero P, Speiser D E. The CD4-like molecule LAG-3, biology and therapeutic applications, Expert Opin Ther Targets 2011; 15:91-101.]

Golden et al., Arteriosclerosis, Thrombosis, and Vascular Biology, 34: A359 (2014) has shown that human homozygous carriers of the SCARB1 rs10846744 risk (CC) allele had significantly lower plasma LAG3 protein levels. In vitro studies revealed that risk (CC) lymphocytes secreted more pro-inflammatory cytokines (TNFα) and less anti-inflammatory cytokines (IL-10) as compared with reference (GG) lymphocytes. Consequently, these same carriers of the risk (CC) allele were shown to have increased carotid intimal media thickness (cIMT), a known surrogate for CVD event risk.

In vitro and in vivo murine studies have suggested that sLAG3 regulates MHC class II signaling pathways to limit T cell activation and homeostasis, while a few clinical studies have shown associations between sLAG3 and tuberculosis resistance [Lienhardt et al, Active tuberculosis in Africa is associated with reduced Th1 and increased Th2 activity in vivo, G. s.l.: Eur J Immunol, 2002, Vol. 32, pp. 1605-1613] and breast cancer prognosis [Triebel et al., A soluble lymphocyte activation gene-2 (sLAG-3) protein as a prognostic factor in human breast cancer expressing estrogen or progesterone receptors. M-F. s.l.: Cancer Letters, 2006, Vol. 235, pp. 147-153]. In murine cells, Kisielow et al reported that activated T cells induced LAG3 expression on B cells. [Kisielow M, Kisielow J, Capoferri-Sollami g, Karjalainen K. Expression of lymphocyte activation gene 3 (LAG-3) on B cells is induced by T cells. Eur J Immunol 2005; 35:2081-2088.] They determined that LAG3 induction on B cells was T cell dependent and not dependent on other stimuli such as unmethylated CpG motif 1826, bacterial LPS, or anti-Ig antibody in combination with anti-CD40 and IL-4. In contrast, LAG3 RNA and protein was detected in EBV-transformed B cells, with significantly higher expression in EBV-transformed cells expressing the reference SCARB1 rs10846744 G allele as compared with cells expressing the risk C allele. Although EBV transformation of B lymphocytes could activate the cells, there was a significant difference in the level of LAG3 expression based on rs10846744 genotype stratification. Importantly, others observed a lack of LAG3 expression in B cells, such as Ramos cells [Baixeras E, Huard B, Miossec C, Jitsukawa S, Martin M, Hercend T, Auffray C, Triebel F, Piatier-Tonneau D., Characterization of the lymphocyte activation gene 3-encoded protein. A new ligand for human leukocyte antigen class II antigens. J Exp Med 1992; 176:327-337.] However, the present inventor genotyped these cells and found that they were heterozygous for the rs10846744 variant. More recently, Morales et al showed that EBV positivity in Hodgkin lymphomas were significantly associated with increased gene expression of LAG3. [Morales O, Mrizak D, Francois V, Mustapha R, Miroux C, Depil S, Decouvelaere A V. Lionne-Huyghe P, Auriauht C, de Launoit Y, Pancre V, Delhem N. Epstein-Barr virus infection induces an increase of T regulatory type 1 cells in Hodgkin lymphoma patients. Br J Haematol 2014 Jul. 9. Epub ahead of print]

Studies with murine models have shown that atherosclerotic lesion size and inflammation are increased when there is a deficiency of inhibitors of T cell activation, including the PD-1/PD-L1 and PD-L2 pathways and regulatory T cells [Adaptive immunity in atherogenesis: new insights and therapeutic approaches. Lichtman A H, Binder C J, Tsimikas S, Witztum J L. s.l.: J Clin Invest, 2013, Vol. 123, pp. 27-36].

Baixeras et al, supra, characterized the cellular distribution of LAG3 in a number of cell lines and demonstrated that LAG3 resided within lipid rafts. Subsequently, Woo et al. reported the intracellular distribution of LAG3 and found that LAG3 was equally distributed between intracellular compartments and the plasma membrane. [Woo S-R, Li N, Bruno T C, Forbes K, Brown S, Workman C, Drake C G, Vignali D A A. Differential subcellular localization of the regulatory T-cell protein LAG-3 and the coreceptor CD4. Eur J Immunol 2010; 40:1768-1777]

By using flow cytometry, the present inventor confirmed that low levels of LAG3 were detected on the cell surface of rs10846744 risk C expressing cells regardless of stimulation conditions. However, LAG3 was expressed on the cell surface in unstimulated rs10846744 reference G cells and its levels increased significantly after stimulation. These results in EBV transformed B cells are in contrast to those reported by Woo et al, supra, in that they reported that LAG3 was expressed on the surface only in activated T cells.

It is also known that lipid raft signaling is essential for B cell activation. [Simons K, Toomre D. Lipid rafts and signal transduction. [Nat Rev Mol Cell Biol 2000; 1:31-39] Specifically, stimulation of the B cell receptor (BCR) initiates phosphorylation of the immunoreceptor tyrosine-based activation motifs (ITAMs) in the cytoplasmic tails of CD79A and CD79B (transmembrane immunoglobulin (Ig) receptor associated with Ig-alpha/Ig-beta heterodimers) [Schamel W W, Reth M. Monomeric and oligomeric complexes of the B cell antigen receptor. Immunity. 2000; 13:5-14] Phosphorylation of ITAMs serve as docking sites for Syk, which is mediated by different Src family kinases (SFKs) including Fyn, Blk, and Lyn [Takata M, Sabe H, Hata A, Inazu T, Homma Y, Nukada T, Yamamura H, Kurosaki T. Tyrosine kinases Lyn and Syk regulate B cell receptor-coupled Ca2+ mobilization through distinct pathways. EMBO J. 1994; 13:1341-9.]. Lyn is the major protein involved in lipid raft signaling upon B cell activation [Simons, supra]. This activation initiates the coordinate assembly of the "signalosome", composed of a variety of intracellular signaling molecules and includes Btk, phosphatidylinositol 3-kinase (PI3K) and PLCγ2 [Blix E S, Irish J M, Husebekk A, Delabie J, Forfang L, Tierens A M, Myklebust J H, Kolstad A. Phospho-specific flow cytometry identifies aberrant signaling in indolent B-cell lymphoma. BMC Cancer 2012:12: 478.] PLCγ2 is the predominant isoform expressed in human B lymphocytes [Coggeshall K M, McHugh J C, Altman A. Predominant expression and activation-induced tyrosine phosphorylation of phospholipase C-gamma 2 in B lymphocytes. Proc Natl Acad Sci USA. 1992; 89:5660-4.] It is also indispensable for BCR-mediated phosphoinositol hydrolysis and the subsequent biochemical events including PKC activation [Sugawara H, Kurosaki M, Takata M, Kurosaki T. Genetic evidence for involvement of type 1, type 2 and type 3 inositol 1, 4,5-trisphosphate receptors in signal transduction through the B-cell antigen receptor. EMBO J. 1997; 16:3078-88].

MHC class II is the main ligand to LAG3, and the latter binds to the former with high affinity where it negatively regulates cellular proliferation, activation, and homeostasis of T cells, and has been reported to play a role in Treg suppressive function. By contrast, signaling through MHC class II in lipid raft microdomains on a subset of dendritic cells after it is bound by soluble LAG3 (sLAG3) results in dendritic cell activation. The inventor has now discovered that cellular LAG3 in lymphocytes is causal in regulating the phosphosignaling cascade. This is a distinct and novel function of LAG3, independent of its previous known function of binding to MHC class II receptors.

However, the major apolipoprotein associated with HDL particles, apoA-1, has been shown to inhibit inflammatory cytokine production by inhibiting activation of monocytes by T lymphocytes [Hyka N, Dayer J-M, Modoux C, Kohno T, Edwards III C K, Roux-Lombard P, Burger D. Apolipoprotein A-I inhibits the production of interleukin-1β and tumor necrosis factor-α by blocking contact-mediated activation of monocytes by T lymphocytes. Blood 2001; 97:2381-2389]. Specifically, Hyka et al. observed that apoA-I inhibited cytokine production from stimulated monocytes by first binding to a surface factor, which suggests the possibility that apoA-I might interact with surface LAG3.

The significant association of SCARB1 variant, rs10846744, with coronary heart disease (CHD) was shown in Manichaikul et al (Arterioscler Thromb Vasc Biol 2012; 32:1991-1999). However, previous analyses do not show that rs10846744 is directly associated with SCA and incident CVD. This is because, as the present inventor has found, LAG3 is an important immune regulator that mediates the association of rs10846744 with atherosclerotic disease and CVD. LAG3 protein expression on effector and regulatory T cells may inhibit T cell receptor (TCR)-mediated activation by blocking TCR interaction with MHC class II, and LAG3 protein on plasmacytoid DCs may indirectly suppress effector T cells by other mechanisms. LAG3 protein deficiency may lead to enhanced inflammasome mediated IL-1β and IL-I 18 production by DCs and macrophages, two cytokines that skew T cell differentiation to inflammatory phenotypes that possess specialized cytokine potential [The interleukin-1 family: back to the future. Garlanda C, Dinarello C A, Mantovani A. s.l.: Immunity, 2013, Vol. 39, pp. 1003-1018].

Therefore, LAG3 protein deficiency in mice (Lag3) and humans (LAG3) is predicted to enhance pro-atherogenic T cell responses to hypercholesterolemia and lead to increased plaque inflammation and/or increased plaque development.

It has not been obvious that deficiency of LAG-3 protein due to genetic variations exists in humans and that it is significantly associated with atherosclerosis, other chronic inflammatory diseases, cardiovascular and/or noncardiovascular mortality. Based on the mediator role that LAG3 plays in CVD and other chronic inflammatory diseases, the present invention discloses a method for using LAG3 expression profiling as a biomarker for assessing patients at risk of CVD based on certain SCARB1 and LAG-3 gene variations and other genetic and non-genetic factors that increase risk for clinically significant atherosclerosis, other chronic inflammatory diseases, chronic inflammatory diseases, dysfunctional HDL, cardiovascular and/or non-cardiovascular morbidity and mortality and for ameliorating said risk with a novel recombinant LAG3 companion therapeutic.

The therapeutic activity of IMP321 (the human dimeric soluble form of LAG3) is well-known in pre-clinical as well as clinical studies. It has been shown that the combination of hLAG3—Ig as an adjuvant with chemotherapeutic agents is superior to either treatment on its own.

Furthermore, a LAG3 blockade may be combined with blockade of other inhibitory receptors, such as PD-1, resulting in enhanced T cell activity and protection from disease. In addition, the therapeutic activity of soluble recombinant dimeric LAG3 protein is also known in several respects. [Sierro et al., "The CD4-like molecule LAG-3, biology and therapeutic applications", Section 3]. In humans, recombinant LAG3 induces DC activation and provides immune adjuvant activity (in contrast to the inhibitory activity of the membrane-bound form of LAG-3). Andreae et al., "Maturation and activation of dendritic cells induced by lymphocyte activation gene-3 (CD223)", J Immunol, 168:3874-80 (2002).

U.S. Pat. No. 6,410,509 to Triebel (Institut Gustave-Roussy) issued Jun. 25, 2002 shows the use of hLAG3 as adjuvant for vaccination and in cancer treatment, the systemic administration of soluble hLAG3 directly inducing an inhibition of in vivo tumor growth (see Example IV). Similarly, United States Patent Application 20110008331 to Triebel (Immutep) published Jan. 13, 2011 shows the periodic use of a recombinant LAG3 to boost a monocyte-mediated immune response, in particular to elicit an increase in the number of monocytes in blood. The application notes the discovery "entirely unexpectedly" that human LAG3 or derivatives thereof when inoculated into patients with highly malignant tumors induced a potent immunity which is monocyte dependent. The induced immunity manifests itself by a significant increase in blood monocyte counts. Despite the use of hLAG3 as a vaccine adjuvant to boost T-cell counts in known cancer patients, no one has yet been motivated to peremptorily screen for a LAG3 deficiency marker and, if found, ameliorate the consequent risk by treating prospective patients with recombinant human LAG3 by periodic administration of at different time points. The present inventor does this by pre-screening patients at risk for cardiovascular disease, other chronic inflammatory diseases, cardiovascular and/or non-cardiovascular morbidity and mortality using specific 2-point expression profiles (combinations of mutations and/or non-genetic causes, e.g., SCARB1 rs10846744 mutation and/or LAG-3 rs870849 or other genetic or non-genetic causes and a mutation), followed by a tailored therapeutic regimen using recombinant human lymphocyte activation gene-3 as a companion therapeutic.

SUMMARY OF THE INVENTION

It is, therefore, an object of the present innovation to provide a novel strategy for assessing patients at risk for cardiovascular disease, other chronic inflammatory diseases, cardiovascular and/or non-cardiovascular morbidity and mortality based on lymphocyte activation gene 3 (LAG3) protein deficiency, and for mediating said risk with a tailored therapeutic regimen including use of recombinant human lymphocyte activation gene-3 as a companion therapeutic.

In one embodiment, the method comprises a first step of qualitatively pre-screening a subject for one or more risk factors for developing cardiovascular disease, a second step of quantitatively detecting a LAG3 protein deficiency in a sample from the subject, and a third step of treating the subject with recombinant human lymphocyte activation gene-3 as a companion therapeutic to one or more agents selected from the group consisting of: an anti-inflammatory agent, an agent that improves HDL-C function, size, and/or composition in the subject, an agent that decreases dysfunctional HDL-C in the subject, PCSK9 inhibitors (a new class of drugs that have been shown to dramatically lower LDL cholesterol levels), or any other cholesterol-lowering biologic, cholesterol altering small molecule, agents that mimic LAG3 function by binding to MHC class II molecules, agents that mimic LAG3 phosphosignaling effects, agents that mimic the role of LAG3 in CD4+, CD8+ T, NK cells, monocytes, dendritic cells, B regs, and Tregs that do or do not bind MHC class II molecules, and agents that mimic the role of LAG3 in lipid rafts of cell membranes. LAG3 mimetics could include small molecule agents, microRNAs, oligonucleotides, biologics, activating antibodies, agents that affect DNA or RNA structure or flexibility that affect LAG3 transcriptional regulation including agents that regulate intracellular cations such as potassium, sodium, lithium, and calcium.

Other objects, features, and advantages of the present invention will become more apparent from the following detailed description of the preferred embodiments and certain modifications thereof.

BRIEF DESCRIPTION OF THE DRAWINGS

The patent or application file contains at least one drawing executed in colors. Copies of this patent or patent application publication with color drawing(s) will be provided by the Office upon request and payment of the necessary fee.

Other objects, features, and advantages of the present invention will become more apparent from the following detailed description of the preferred embodiments and certain modifications thereof when taken together with the accompanying drawings in which:

FIG. 2 is a graph of sLAG3 association with small HDL particles by NMR spectroscopy.

FIG. 4 lists accession numbers and sequence listings for suitable recombinant human LAG3, which can be either in monomeric or dimeric form.

FIG. 5 Table 2 shows multivariable regression analyses of independent predictors for plasma LAG-3 (A) and HDL-C (B): MESA.

FIG. 12 is a composite of tables (Tables 3-6) of multi-variable regression analyses.

DETAILED DESCRIPTION OF THE PREFERRED EMBODIMENT

Figure 1:
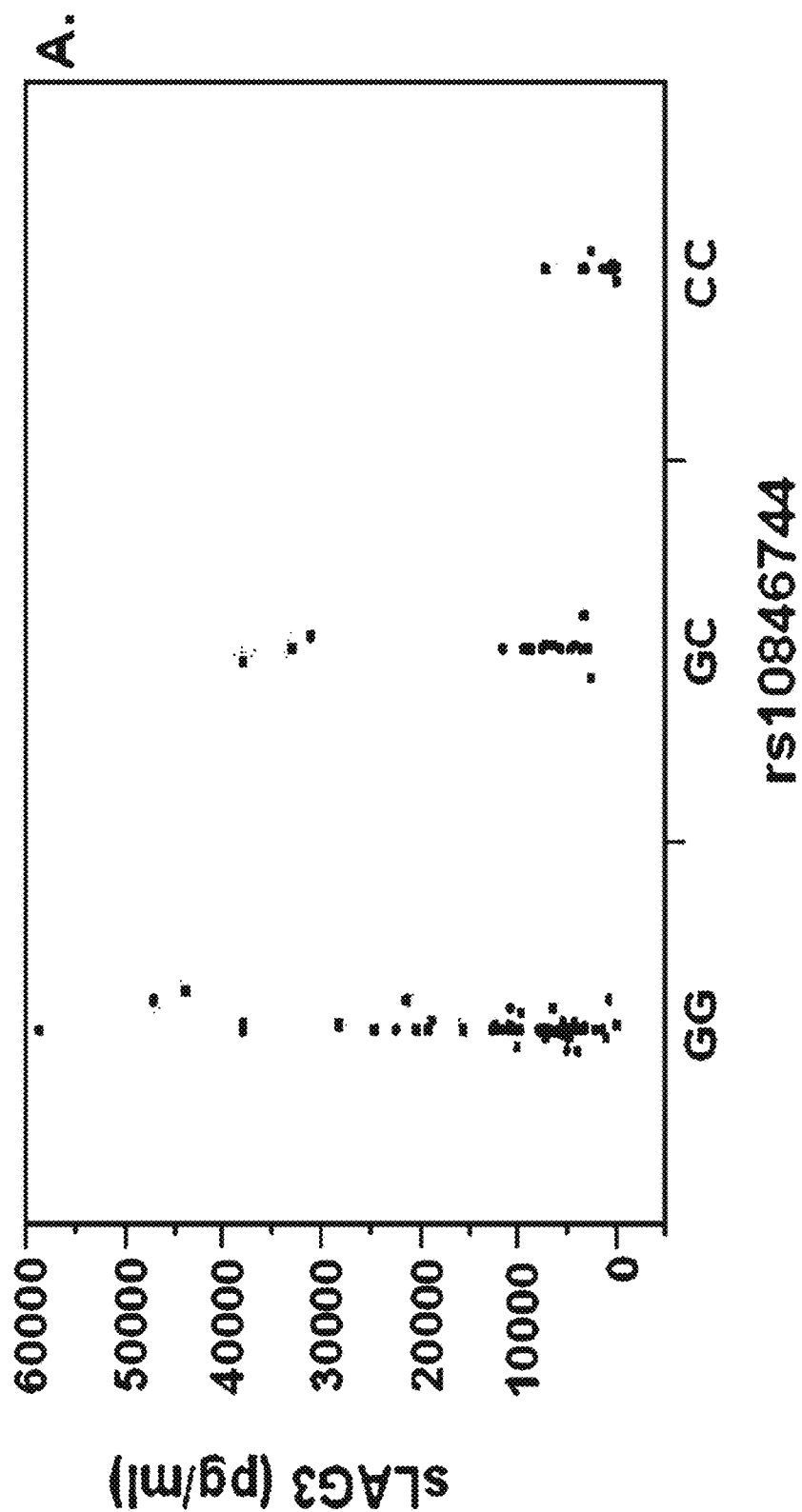
FIG. 1 is a graph of plasma sLAG3 levels significantly associated with SCARBI rs 10846744.

The present invention provides novel methods and kits for determining whether a subject has or is predisposed to atherosclerosis, chronic inflammatory disease, Incident Cardiovascular Disease (ICD), other pathologies characterized by an inflammatory response, cardiovascular and/or non-cardiovascular morbidity and mortality, and for ameliorating the risk by a tailored therapeutic regimen using recombinant human lymphocyte activation gene-3 as a companion therapeutic with one or more agents selected from the group consisting of an anti-inflammatory agent, an agent that improves HDL-C function, size, and/or composition in the subject and an agent that decreases dysfunctional HDL-C in the subject, and/or agents that mimic all the functions of LAG3.

As used herein, the singular forms "a," "an," and "the" include the plural reference unless the context clearly dictates otherwise. Thus, for example, a reference to a "protein" is a reference to one or more proteins, and includes equivalents thereof known to those skilled in the art. Any and all references to a SNP by the "rs" designation, for example rs10846744 hereby incorporates the associated nucleotide sequence which is easily retrievable by known methods. Specifically, the nucleotide sequence for rs10846744 is retrievable, for example, from NCBI's dbSNP Entrez database. SCARB1 refers to the HDL-receptor gene, scavenger receptor class B type 1 (SCARB1), and LAG3 means the immune checkpoint inhibitor, Lymphocyte Activation Gene-3 (LAG-3). The term "adjuvant" is herein defined as a substance that enhances the body's immune response to an antigen.

Discovery Data

LAG3 is transcriptionally controlled by the SCARB1 rs10846744 variant and by LAG3 SNPs and cellular metabolic changes. Specifically, a polymorphism that occurs in the coding sequence of the SCARB1 and/or LAG3 genes can be used as a diagnostic predictor of pathologies such as infection, inflammation, chronic inflammatory disease, coronary artery disease, cardiovascular and/or non-cardiovascular morbidity and mortality. The present inventor has used RNA sequencing to identify the immune modulator LAG3 as playing a major role in the causal pathway linking the association of the SCARB1 intronic variant, rs10846744, with subclinical atherosclerosis and incident CVD. Validation experiments confirmed the significant association of SCARB1 rs10846744 with LAG3. The experiments observed significantly lower levels of sLAG3 in the culture media from rs10846744 risk C expressing cells as compared to the rs10846744 reference G cells. Thus, the different methodologies confirmed that less LAG3 protein was expressed in the rs10846744 risk C cells. The inventor then examined what effect, if any, the lack of LAG3 might have on the downstream signaling pathway in EBV-transformed B cells. The results clearly showed significant differences in lipid raft signaling between rs10846744 risk C and rs10846744 reference G expressing cells. The absence of phosphorylation of CD79A in the rs10846744 C risk allele indicates that impairment of LAG3 to the membrane causally inhibits the interaction between the receptors initiating proximal and downstream signaling, further indicating the critical role of LAG3 in B cell activation. Importantly, overexpressing or silencing LAG3 confirmed the causal role of LAG-3 in downstream signaling, a new observation identified by the inventor. Combining data derived from RNA-sequencing and the in vitro studies of LAG3 from the EBV-transformed B cells, and with the knowledge that surface LAG3 was cleaved to generate sLAG3, the present inventor explored whether plasma sLAG3 levels would be significantly different between carriers of the rs10846744 variant.

FIG. 1 is a graph of plasma sLAG3 levels significantly associated with SCARB1 rs10846744, and shows a significant difference in plasma sLAG3 levels between HALP carriers of the rs10846744 reference GG vs. rs10846744 risk CC allele. Within the field of atherosclerosis there was no previous associations of HDL lipoproteins and/or subfractions with LAG3 or sLAG3.

There was no observed association of plasma apoA-I with rs10846744 or sLAG-3 but did find a significant association of these variables with small HDL particles.

FIG. 2 shows sLAG3 significantly associated with small HDL particles by NMR spectroscopy. sLAG3 levels were inversely associated with small HDL particles in fasting plasma samples from HALP subjects. This data was not stratified by carrier status for rs10846744 (P=0.01, r=0.27, n=81). Also, small dense HDL particles, which are enriched in apoA-I and cholesterol poor, have been positively associated with increased risk for CHD in a number of large clinical studies. Cellular LAG3 expression and function were significantly reduced in cells isolated from carriers of the rs10846744 risk C allele. More importantly, circulating sLAG3 levels were significantly lower in these same carriers as measured in the HALP. In conclusion, LAG3, an important immune regulator, has been identified as being transcriptionally controlled by the rs10846744 variant, as well as by LAG3 rs870849 and non-genetic causes.

The Diagnostic Method

Generally, the present method entails a two-prong diagnostic, beginning with a qualitative pre-screening as to whether a subject has or is predisposed to atherosclerosis, chronic inflammatory disease, Incident Cardiovascular Disease (ICD), cardiovascular and/or non-cardiovascular morbidity and mortality, and other pathologies characterized by an inflammatory response by symptomatic expression of same or based on non-genetic causes. Given a qualitative indication, the diagnostic continues to a quantitative inquiry based on a blood sample. The sample may be analyzed by assay or by genetic testing. More specifically, LAG3 protein deficiency can be determined by plasma, serum, or other biological fluid measurements using ELISA assays or other protein assays determined by those skilled in the art. Alternatively, LAG3 protein deficiency can be determined by measurement of SCARB1 mutations, such as rs10846744 or LAG3 rs870849, other SNPs/insertions/deletions, or non-genetic causes that adversely affect expression and function of LAG3 protein. Genetic screening of a biological sample from a subject is needed to determine the presence of specific allelic variants of one or more polymorphic regions of an SR-BI gene conducted to determine the presence of the underlying SCARB1 mutation rs10846744. SR-B1 (SCARB1) is the predominant receptor for HDL cholesterol and plays an important role in reverse cholesterol transport (removal from cells with eventual disposal via the liver). SR-B1 is highly expressed in the liver and steroidogenic tissues such as the ovary. SR-B1 is thought to be critical in maintaining cholesterol stores for steroid production. Given an expression profile comprising marker combinations of 1) non-genetic causes plus 2) assay/mutation, a positive pre-screening indication is followed by a tailored therapeutic regimen (below) using recombinant lymphocyte activation gene-3 as a companion therapeutic.

Figure 3:
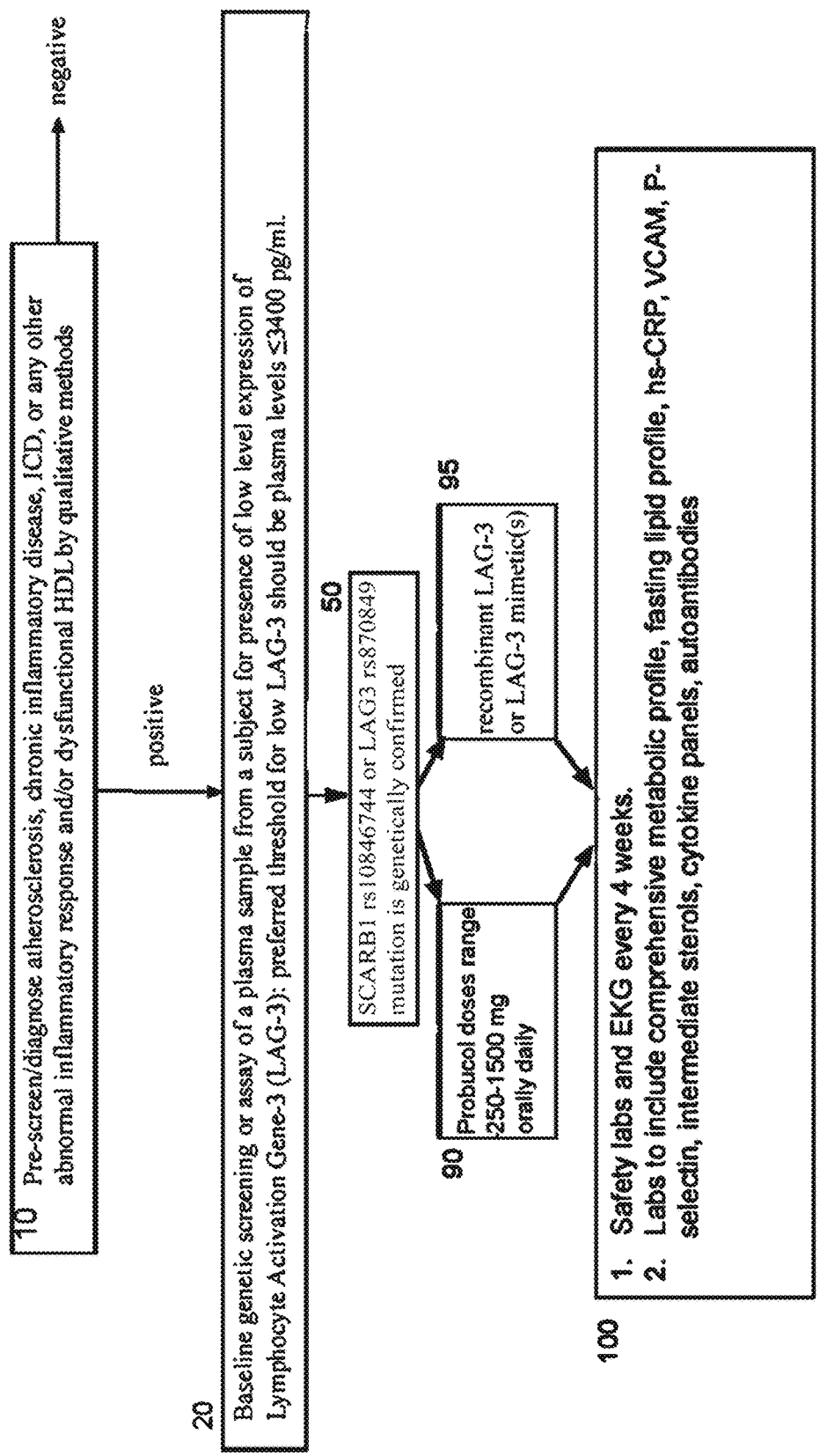
FIG. 3 is a block diagram of an exemplary embodiment of the present diagnostic method.

FIG. 3 is a block diagram of an exemplary embodiment of the present diagnostic method, which begins at step 10 with an initial pre-screening/qualitative diagnosis of a subject for symptoms and/or non-genetic causes predisposition to atherosclerosis, chronic inflammatory disease, Incident Cardiovascular Disease (ICD), cardiovascular and/or non-cardiovascular morbidity and mortality, experience of heart attack while taking statins or other cholesterol lowering medications, or any other pathology characterized by an inflammatory response, abnormal expression of inflammasomes and/or dysfunctional HDL.

Given an initial positive pre-screening, at step 20 a baseline protein assay and/or genetic screening of a plasma or serum sample from a subject for presence of low level expression of Lymphocyte Activation Gene-3 (LAG-3) is conducted. LAG3 expression is measured and compared to a baseline threshold for low LAG3 should be plasma levels ≤3400 pg/ml. This LAG3 expression profiling provides a positive biomarker for further assessment of inflammasomes, chronic inflammatory diseases and dysfunctional HDL. The proinflammatory state due to LAG3 deficiency provides a novel protein biomarker for diseases associated with chronic inflammation, including autoimmune disease, atherosclerosis, type 2 diabetes mellitus, age-related macular degeneration, and Alzheimer's disease. Murine and human lymphocyte activation gene-3 assays may be conducted by Murine Lag3 and human LAG3 ELISA kits, which are commercially available.

At step 50, and given the double-positive indication of suspected presence of the SCARB1 rs10846744 or LAG3 rs870849 mutation, the patient's underlying SCARB1 rs10846744 or LAG3 rs870849 mutation is genetically confirmed. The presence of the SCARB1 rs10846744 or LAG3 rs870849 mutation can be confirmed by a variety of known methods including genotyping. Genotyping may be carried out by direct mutation analysis by DNA sequencing of a standard blood test. Genomic DNA is prepared from a whole blood sample purified to isolate DNA from the blood sample. The purity and quantity of DNA may be checked by spectrophotometry. The DNA is added to a plate and genotyped with an oligo-ligation assay (for example, SNPlex® is a suitable platform for SNP genotyping sold by Applied Biosystems of Foster City, Calif., USA) following manufacturer guidelines. The oligo-ligation assay uses fluorescent dye-labeled probes to indicate presence of the SCARB1 rs10846744 mutation or LAG3 rs870849 mutation. Other methods useful in screening for the presence of a specific allelic variant of one more polymorphic regions of an SR-B1 gene include, for example, DNA sequencing, hybridization techniques, PCR based assays, fluorescent dye and quenching agent-based PCR assay (Taqman PCR detection system), RFLP-based techniques, single strand conformational polymorphism (SSCP), denaturating gradient gel electrophoresis (DGGE), temperature gradient gel electrophoresis (TGGE), chemical mismatch cleavage (CMC), heteroduplex analysis based system, techniques based on mass spectroscopy, invasive cleavage assay, polymorphism ratio sequencing (PRS), microarrays, a rolling circle extension assay, HPLC-based techniques, DHPLC-based techniques, oligonucleotide extension assays (OLA), extension based assays ARMS (Amplification Refractory Mutation System), ALEX (Amplification Refractory Mutation Linear Extension), SBCE (Single base chain extension), a molecular beacon assay, invader (Third wave technologies), a ligase chain reaction assay, nuclease assay-based techniques, hybridization capillary array electrophoresis (CAE), pyrosequencing, protein truncation assay (PTT), immunoassays, haplotype analysis, and solid phase hybridization (dot blot, reverse dot blot, chips), etc. One type of screening method is allele specific hybridization using probes overlapping the polymorphic site and having about 5, 10, 20, 25, or 30 nucleotides around the polymorphic region. In one embodiment of the invention, several probes capable of hybridizing specifically to allelic variants are attached to a solid phase support, e.g., a "chip". Oligonucleotides can be bound to a solid support by a variety of processes, including lithography. Indeed, a chip can hold up to 250,000 oligonucleotides (GeneChip®, Affymetrix®).

In one embodiment, a chip comprises all the allelic variants of at least one polymorphic region of the SCARB1 and/or LAG3 genes. The solid phase support is then contacted with a test nucleic acid and hybridization to the specific probes is detected. Accordingly, the identity of numerous allelic variants of one or more genes can be identified in a simple hybridization experiment.

In some screening methods it is necessary to first amplify at least a portion of the SCARB1 or LAG3 gene prior to identifying the allelic variant. Amplification can be performed, e.g., by PCR, according to methods known in the art. In one embodiment genomic DNA of a cell is exposed to two PCR primers and amplification for a number of cycles sufficient to produce the required amount of amplified DNA. Because SNPs constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms. The methods described herein may be performed, for example, by utilizing pre-packaged diagnostic kits, such as those described above, comprising at least one probe or primer nucleic acid described herein, which may be conveniently used, e.g., to determine whether a subject has or is at increased risk of developing a disease associated with a specific SCARB1 and/or LAG3 allelic variant. The methods of the present invention, including methods for identifying the presence of an allelic variant or SNP in the SR-B1 gene of a subject may be combined with other information or parameters using the methods well known in the art to aid in the identification of subject with deficiency in the LAG3 protein.

Given confirmation, at step 90 the present method initiates a therapeutically-effective regimen of the cholesterol medication probucol, in combination and simultaneous to a regimen of recombinant LAG3 at step 95. The recombinant LAG3 is recombinant human LAG3, either full-length or soluble truncated form as described below, or a LAG-mimetic. As a companion therapeutic, the LAG3 or LAG3 mimetic works in synergy with the cholesterol medication to treat patients found to have LAG3 protein deficiency. The LAG3 mimetic may be any suitable agent that that mimics LAG3 function including small molecule agents, microRNAs, oligonucleotides, biologics, activating antibodies, agents that affect DNA or RNA structure or flexibility, or agents that affect LAG3 transcriptional regulation including agents that regulate intracellular cations such as potassium, sodium, lithium, and calcium. It is possible to replicate the function of Lymphocyte Activation Gene-3 (LAG3) by expressing the recombinant protein that mimics the properties of specific naturally occurring human LAG3 protein by constructing expression vectors that include LAG3 sequences from the specific naturally occurring human LAG3 sequences. For purposes of the present description the term "LAG3 mimetic" includes these synthetic LAG3 proteins as well as any other known molecules or agents that mimic LAG3 phosphosignaling effects, agents that mimic the role of LAG3 in CD4+ T cells, CD8+ T cells, monocytes, B cells and NK cells that do or do not bind MHC class II molecules, and agents that mimic the role of LAG3 in lipid rafts of cell membranes. An exemplary regimen of probucol treatment may comprise three-to-four months of low-dose treatment (250 mg/day), and even more preferably comprises one-to-two months of said treatments. Treatment strategies used in combination with the LAG3 diagnostic testing include state-of-the-art therapies related to autoimmune diseases, atherosclerosis, dyslipidemia, cardiovascular disease, type 2 diabetes mellitus, age-related macular degeneration and Alzheimer's disease. For example, the present method initiates therapeutically-effective regimens of the cholesterol medication probucol at step 30. An exemplary regimen of probucol treatment may comprise three-to-four months of low-dose treatment (250 mg/day), and even more preferably comprise one-to-two months of said treatments.

The recombinant LAG3 may be Murine Lag3 or Human LAG3 protein, or a LAG3 mimetic either chemically synthesized as the full-length intact 521 amino acid protein or as the truncated soluble form measured in plasma, serum, or other biological fluids. The chemical synthesis must be performed such that no insertions, deletions, premature stop codons, or missense mutations are introduced that materially affect the expression and function of the normal protein. Accession numbers and sequence listings are shown in FIG. 4. The LAG3 companion therapeutic or LAG3 mimetic may be administered by intravenous infusion, SQ injection, SQ infusion via external pump, implantable pump (i.e. peritoneal insulin pumps), intramuscular, inhalation, intranasal, intraventricular, suppositories (vaginal and/or rectal), topical creams, topical gels, topical patches, spinal, sublingual, oral, gastric lavage, pulmonary lavage. Delivery may be in pure form or with excipients, including Ig, albumin, glycosylation, pegylation etc.

Finally, at step 100 monitoring comprises monthly safety labs with comprehensive profiles and EKGs to determine effect on LDL oxidation and on plasma-HDL cholesterol and plasma/serum cytokines. One skilled in the art will readily understand that other suitable therapeutic strategies may be employed to treat these genetically and non-genetically screened individuals including, but not limited to, any other cholesterol and triglyceride modifying medications, progestational and estrogen and estrogen-like medications, as well as medications similar to probucol for lowering HDL cholesterol levels and as antioxidants. Treatments with recombinant human LAG3 with or without other therapeutic agents would be expected to be life-long therapies.

Without further elaboration, it is believed that one skilled in the art, using the preceding description, can utilize the present invention to the fullest extent. To ensure this, an example is given below.

EXAMPLE 1

Materials and Methods

Community dwelling adults between the ages of 18-80 years with fasting plasma HDL-C levels ≥60 mg/dl (HALP) were enrolled in a clinical study. The population was middle-aged and predominantly white females. At the time of enrollment none of the study subjects were treated with cholesterol lowering medications whether prescribed or over-the-counter. Subjects consented to provide overnight fasting blood samples for analysis of lipid profile, DNA analysis for SCARB1 genotyping, and lymphocyte isolation from buffy coats. One-way analysis of variance was used for multiple comparisons of categorical covariates, and Student's t-test for two sample analysis. To assess the effect of time as a continuous variable, quadratic polynomial regressions were performed with time as the dependent factor. Probability values ≤0.05 were considered statistically significant. The frequency of the homozygous rs10846744 variant was similar to rates previously described in multi-ethnic studies of atherosclerosis. Transcriptome analysis reveals differential expression of LAG3. Since rs10846744 resides within a regulatory region of SCARB1 as shown by a bioinformatic screen of the ENCODE database [http://genome.ucsc.edu/] The inventor first examined whether transcriptional differences existed between the rs10846744 reference GG and the risk CC allele expressing B cells cultured under basal (unstimulated) conditions. Since rs10846744 is on the long arm of chromosome 12 we examined for transcriptional differences of targets also residing on chromosome 12 (cis). Five gene transcripts were significantly downregulated and 3 gene transcripts upregulated in rs10846744 risk CC cells as compared with the rs10846744 reference GG cells. In addition to transcriptome differences on chromosome 12, we also observed interchromosomal transcriptional differences ( ) that included significant up-regulation of intracellular inflammasome markers, such as NLRP3 (trans). LAG3 expression is significantly lower in rs10846744 risk C expressing cells. In order to measure changes in cell surface LAG3 expression following activation, cells were first incubated with and without phorbol myristate acetate (PMA)/ionomycin+interleukin-4 (IL-4) and then LAG3 was measured by flow cytometry.

Figure 6:
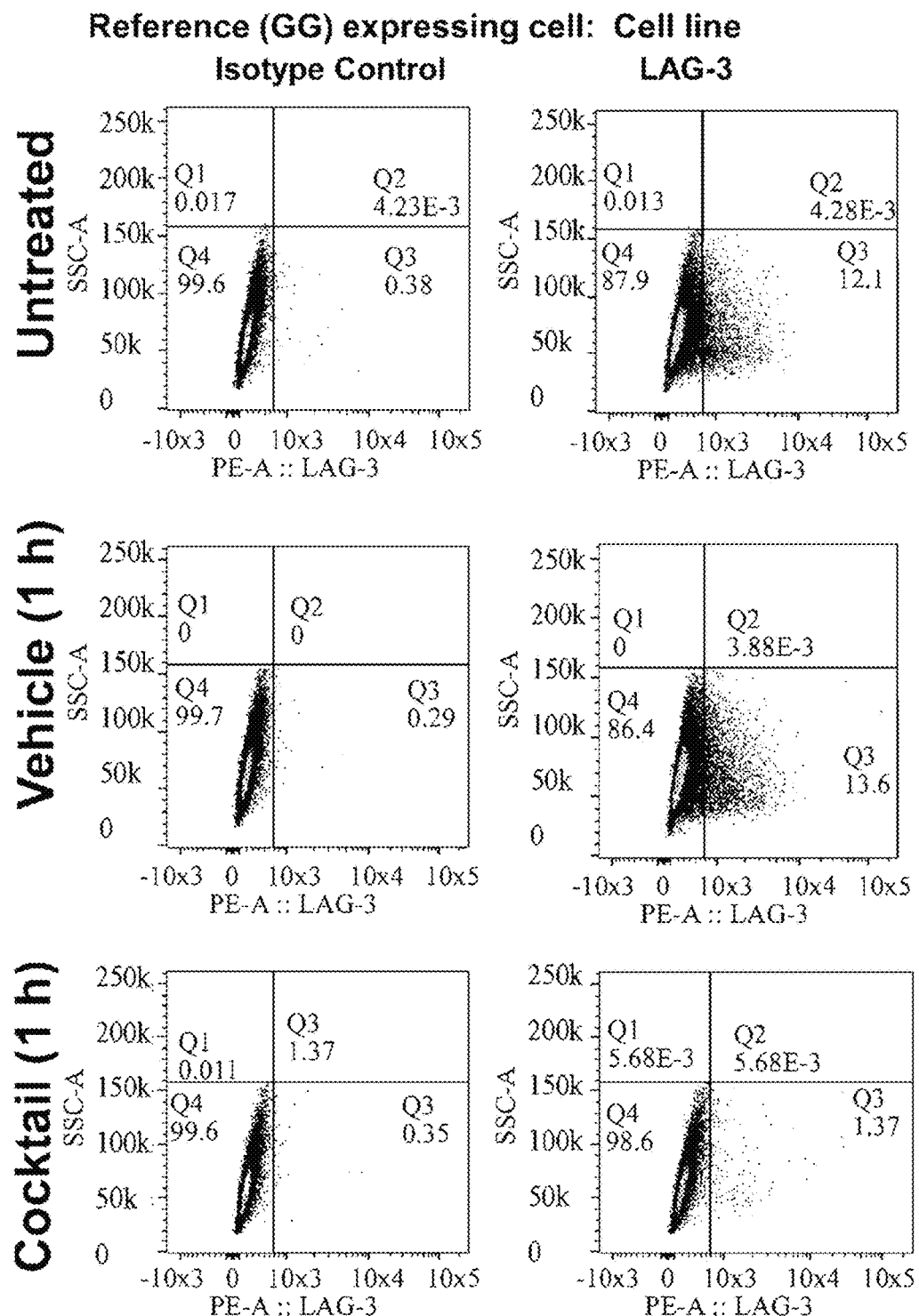
FIG. 6 is a. cytogram graph of the cell surface expression of LAG3in rs10846744 reference G and rs10846744 risk C expressing cells measured by flow cytometry.
Figure 6:
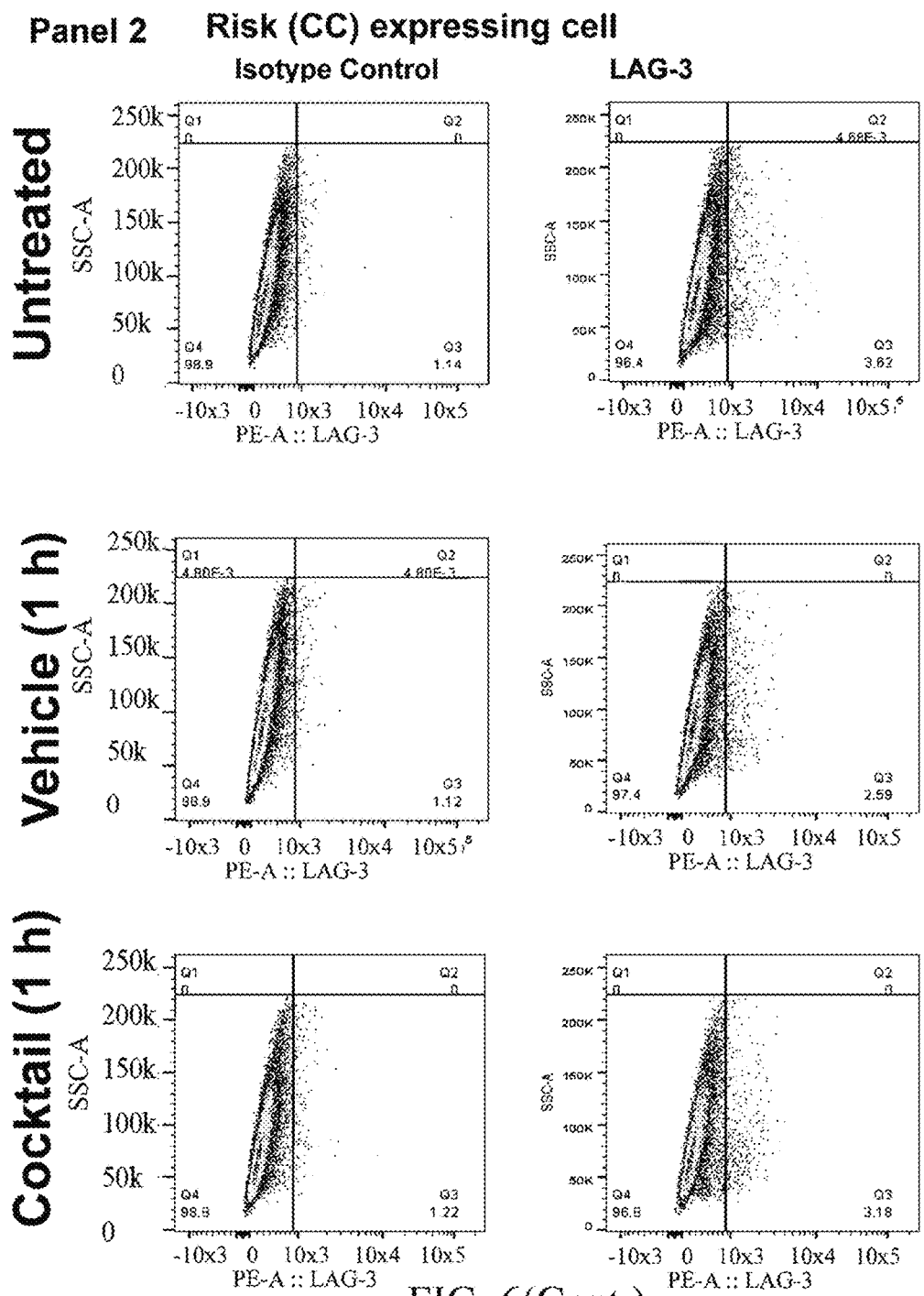
Figure 6:
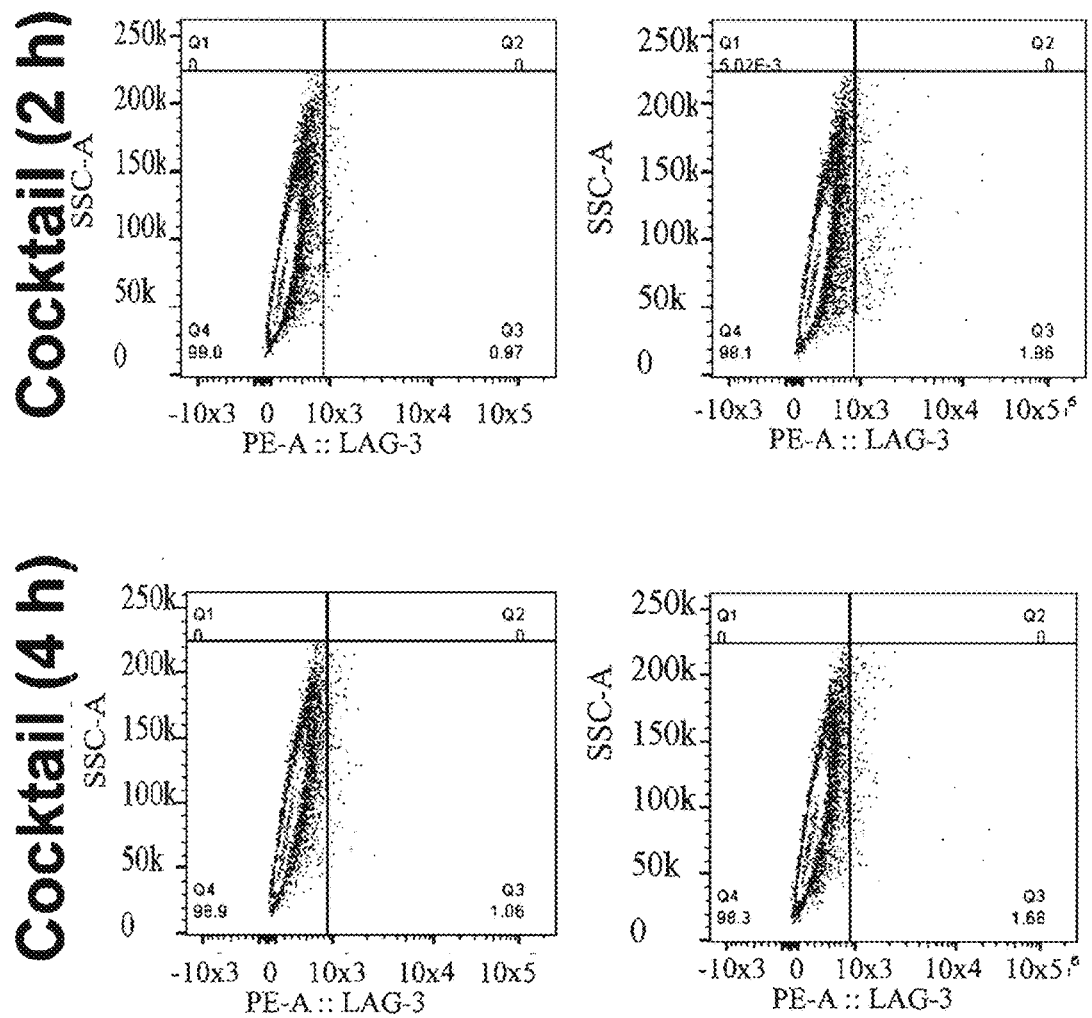
Figure 6:
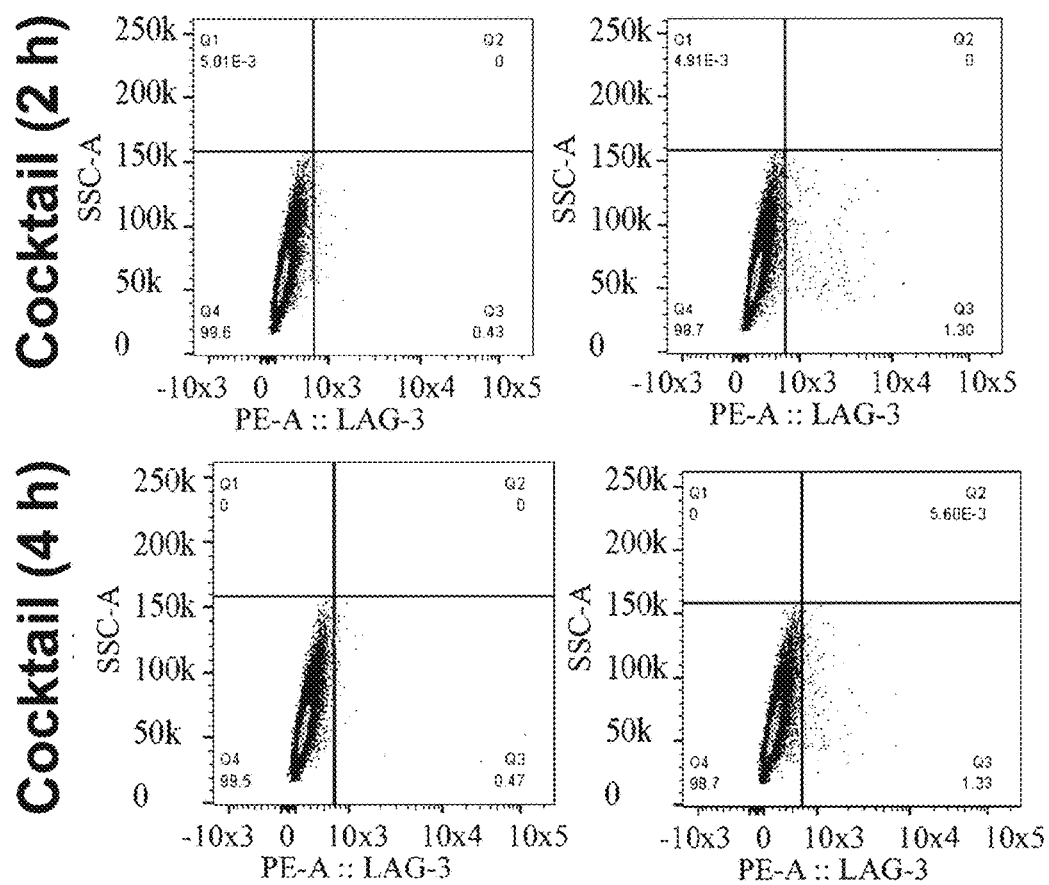

FIG. 6 plots the differential expression of LAG3 in rs10846744 reference G and rs10846744 risk C expressing cells using flow cytometry. Transformed B lymphocytes homozygous for the rs10846744 reference G or rs10846744 risk C alleles were incubated under basal or stimulated cocktail (phorbol ester 500 ng/ml, ionomycin 250 ng/ml, and IL-4 100 U/ml) conditions for 0-4 h and stained with isotype control or anti-LAG3 antibodies for measurement of cell surface LAG3 protein, and then fixed for flow cytometry.

panel I: rs10846744 reference G-003 cells under basal and stimulated conditions stained with isotype control or LAG3 antibodies; the data is representative of three independent experiments;

panel II: rs10846744 risk C-008 cells under basal and stimulated conditions stained with isotype control or LAG3 antibodies; the data is representative of three independent experiments.

Figure 7:
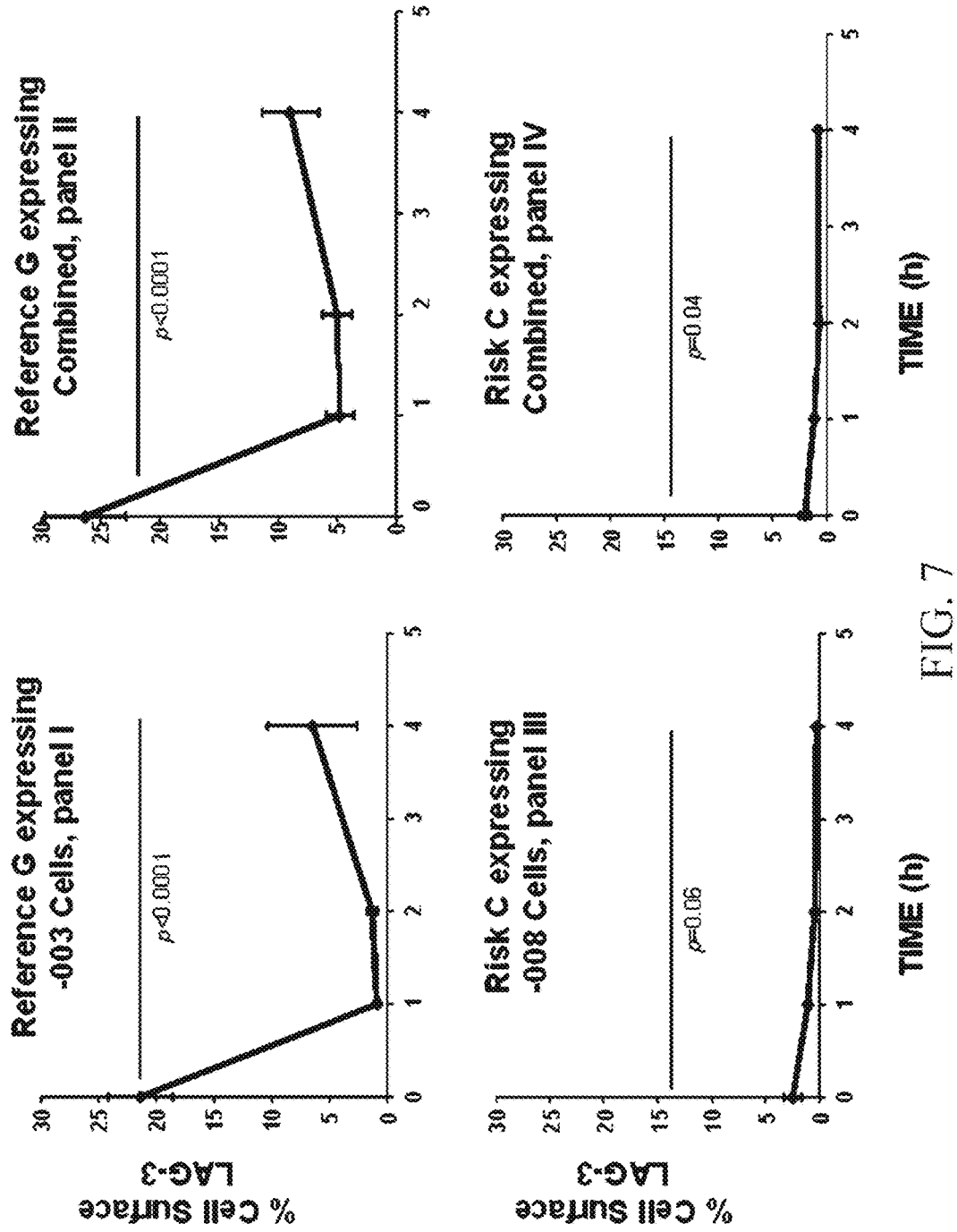
FIG. 7 is a graphic analysis of cell surface expression of LAG3+rs10846744 reference G and risk C expressing cells as measured by flow cytometry.

FIG. 7 is a graphic analysis of cell surface expression of LAG3+ cells as measured by flow cytometry.

Panel I represents pooled data (mean±SE) of three independent experiments from the rs10846744 reference G-003 cell lines, each experiment performed with triplicates (n=9, p<0.0001 compared with baseline).

Panel II represents pooled data (mean±SE) from all the rs10846744 reference G cell lines (n=18, p<0.001 compared with baseline).

Panel III represents pooled data (mean±SE) of three independent experiments from the rs10846744 risk C-008 cell lines, each experiment performed with triplicates (n=9, p=0.06). Panel IV represents pooled data (mean±SE) from all the risk C cell lines (n=15, p=0.04).

Figure 8:
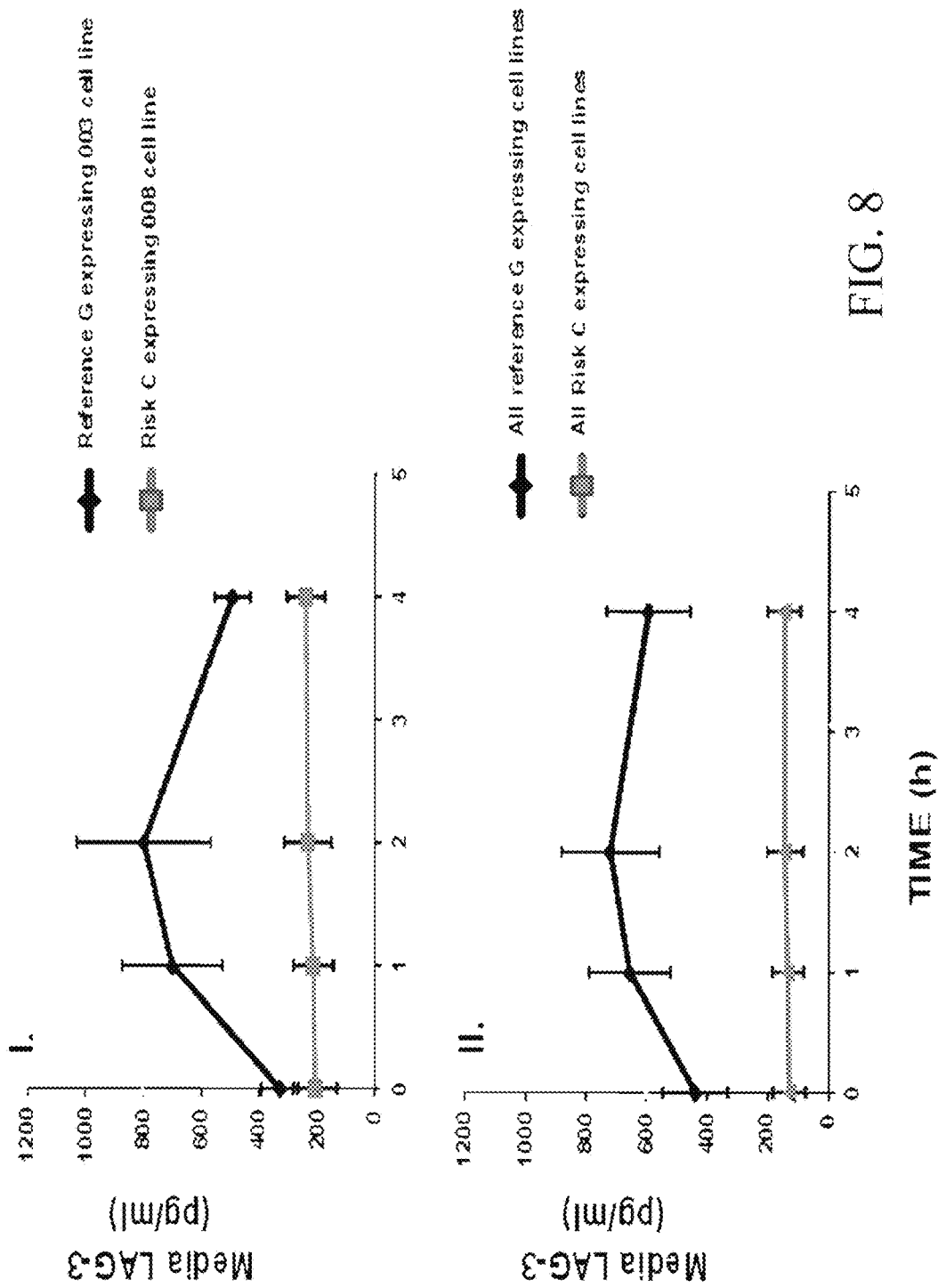
FIG. 8 is a graph of the changes in LAG3 protein levels in the media over time following activation from rs0846744 reference G and rs10846744 risk C expressing cells.

FIG. 8 is a graph of the changes in LAG3 protein levels in the media over time following activation from rs10846744 reference G and rs10846744 risk C expressing cells.

Panel I represents pooled data (mean±SE) of three independent experiments from the rs10846744 reference G-003 cell lines, each experiment performed with triplicates (n=9, p<0.0001 compared with baseline), and from pooled data (mean±SE) of three independent experiments from the rs10846744 risk C-008 cell lines, each experiment performed with triplicates (n=9, p=0.06).

Panel III represents pooled data (mean±SE) from all the rs10846744 reference G cell lines (n=18, p<0.0001 compared with baseline) and pooled data (mean±SE) from all the rs10846744 risk C cell lines (n=15, p=0.04).

Figure 9:
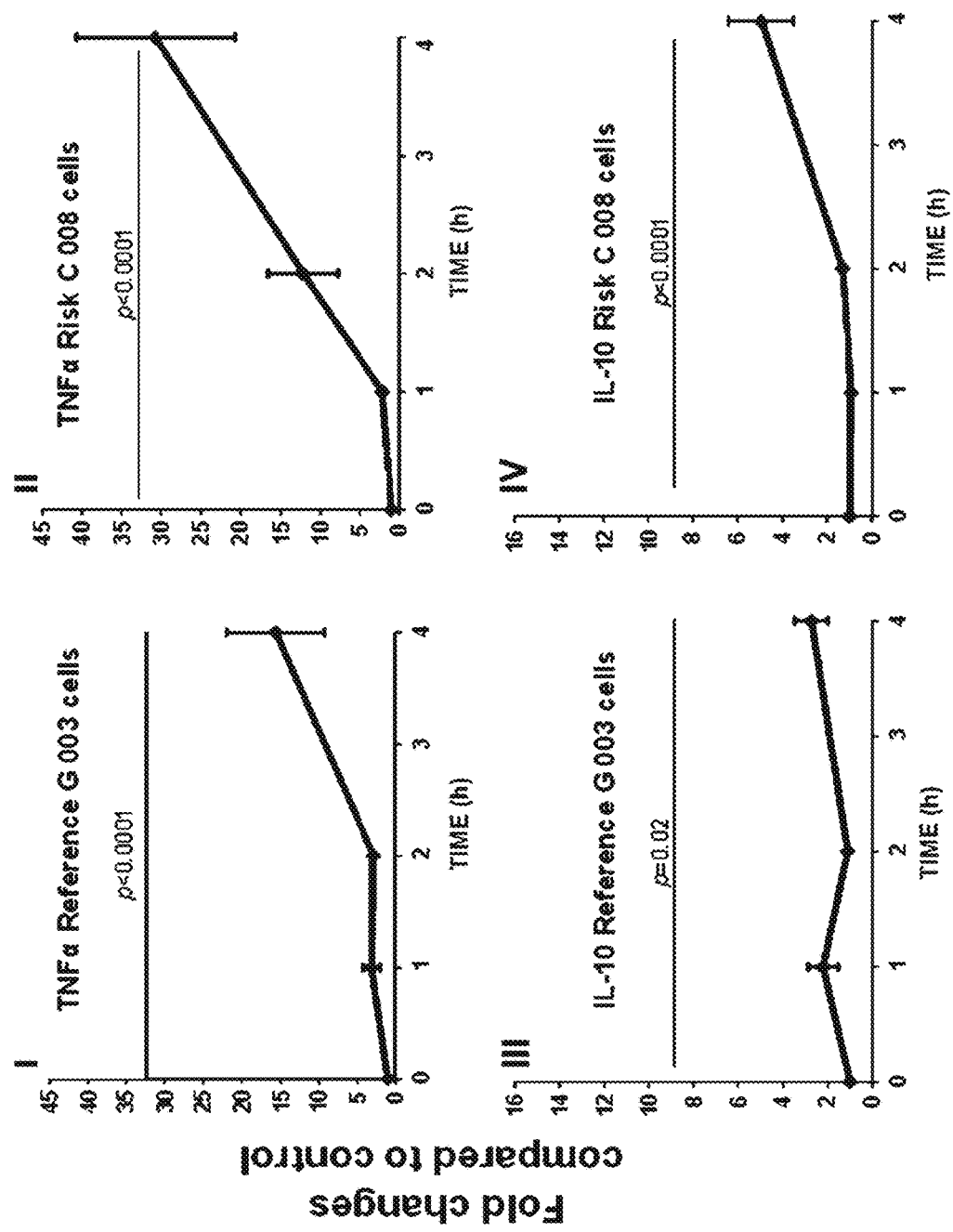
FIG. 9 is a graph of changes in secreted cytokine (TNFα and IL-10) levels in the media over time following activation in rs10846744 reference G-003 and rs10846744 risk C-008 expressing cells.

FIG. 9 is a graph of changes in secreted cytokine (TNFα and IL-10) levels in the media over time following activation in rs10846744 reference G-003 and rs10846744 risk C-008 expressing cells.

Panel I represents TNFα pooled data (mean±SE) of three independent experiments from the rs10846744 reference G-003 cell lines, each experiment performed with duplicates (n=6, p<0.0001 compared with baseline).

Panel II represents TNFα pooled data (mean±SE) of three independent experiments from the rs10846744 risk C-008 cell lines, each experiment performed with duplicates (n=6, p<0.0001 compared with baseline). Panel III represents Il-10 pooled data (mean±SE) from the rs10846744 reference G-003 cell lines, each experiment performed with duplicates (n=6, p=0.02 compared with baseline), while Panel IV represents IL-10 pooled data (mean±SE) of three independent experiments from the rs10846744 risk C-008 cell lines, each experiment performed with duplicates (n=6, p<0.0001).

Referring collectively to FIGS. 6-9, at baseline, cell surface expression of LAG3 was 92% lower in the rs10846744 risk C expressing cells (2.02±2.8) as compared with rs10846744 reference G cells (26.3±2.6, p<0.0001). Following stimulation with PMA/ionomycin+IL-4, as compared with baseline levels, over time cell surface LAG3 expression decreased significantly in rs10846744 reference G (p<0.0001, 003 cell line and all combined) and rs10846744 risk C expressing cells (p=0.06 for 008 cells and p=0.04 for all combined) (FIG. 7). In parallel, over time, LAG3 levels increased in the medium from the rs10846744 reference G-003 cells (p=0.03, panel I) as compared with no changes observed in the rs10846744 risk C-008 expressing cells (FIG. 8). However, there were no statistically significant differences in LAG3 media levels when comparing combined rs10846744 reference G vs. rs10846744 risk combined C expressing cells (FIG. 8, panel II). Over time TNFα and IL-10 levels in the medium were significantly higher in rs10846744 risk C expressing 008 cells as compared with rs10846744 reference G expressing 003 cells (FIG. 9).

Figure 10:
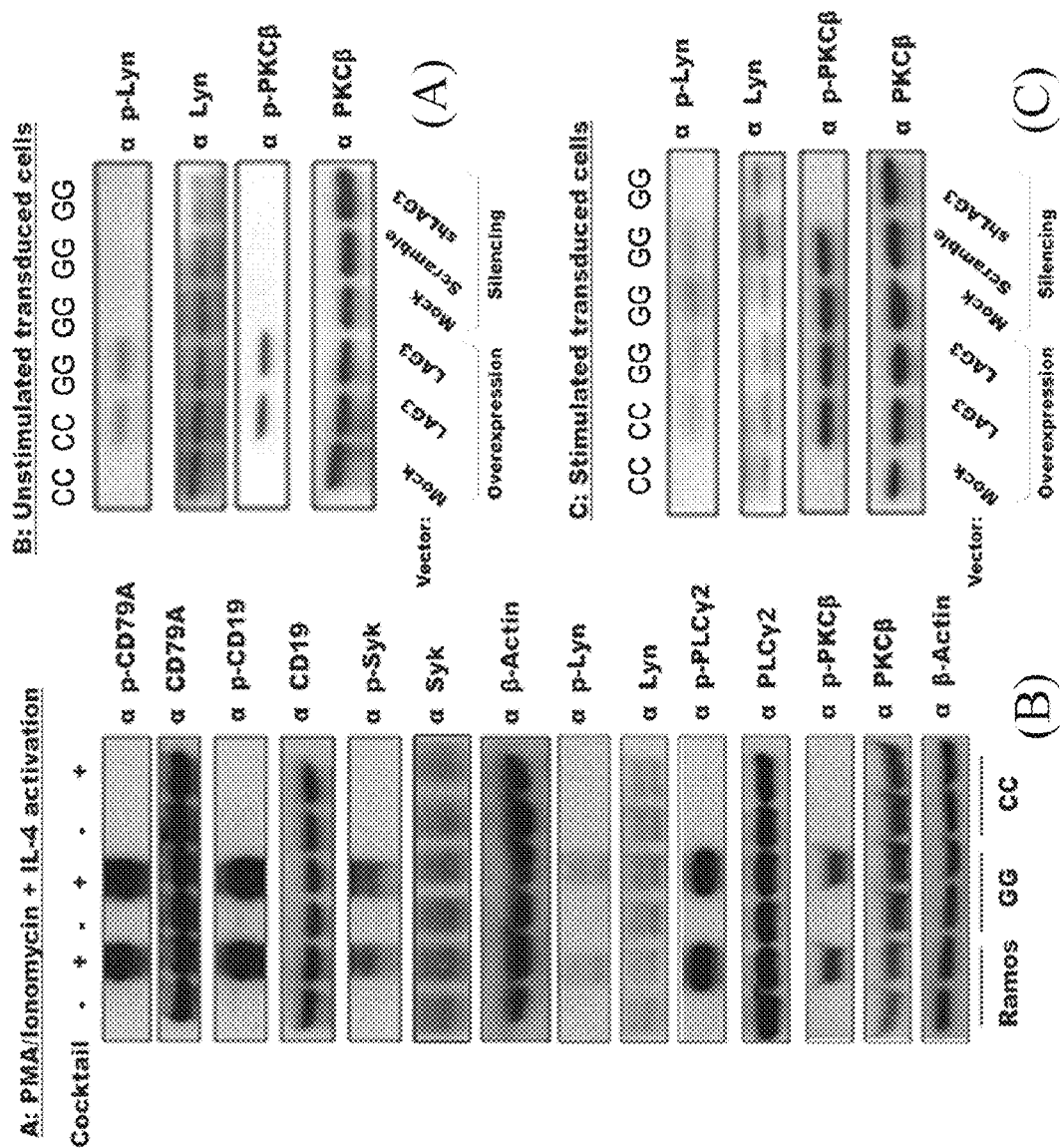
FIG. 10 is a composite figure ((A), (B) and (C)) illustrating how LAG3protein is crucial in BCR signaling, and is causal in affecting phosphosignaling.

FIG. 10 illustrates how LAG3 is crucial in BCR signaling. Whole cell lysates were isolated from transformed B cells expressing the rs10846744 reference G or rs10846744 risk C alleles under basal or cocktail stimulated (phorbol ester 500 ng/ml, ionomycin 250 ng/ml, and IL-4 100 U/ml) conditions for 2 h. Reactions were terminated by the addition of an equal volume of lysis buffer and blotted with the indicated total and phospho-antibodies. The results shown are from one representative experiment of 3 replicate pooled samples.

FIG. 10(A): Ramos cell line, GG (003) or CC (008) cells: Stimulated G allele cells, phosphosignaling normalized to corresponding total protein, p-CD79A (p=0.04), p-CD19 (p=0.04), p-Syk (p=0.005), p-Lyn (p=0.001), p-PLCγ2 (p=0.004) and p-PKCβ (p=0.003) as compared with unstimulated conditions in the reference G allele cells.

FIG. 10(B): BCR signaling and overexpression of lentiviral LAG3-GFP or shRNA-LAG3 in unstimulated cells: CC cells p-Lyn (p=0.04); p-PKCβ (p=0.03) and GG cells p-Lyn (p=0.04); p-PKCβ (p=0.01) as compared to cells expressing the Mock vector in the respective allele.

FIG. 10(C): BCR signaling and overexpression of lentiviral LAG3-GFP or shRNA-LAG3 in stimulated cells: CC cells, p-Lyn (p=0.01); p-PKCβ (p=0.01) in stimulated cells as compared to stimulated cells expressing the Mock vector in the risk C allele. Short-hairpin RNA to knockdown LAG3 in GG cells, p-Lyn (p=0.002); p-PKCβ (p=0.009) in stimulated cells as compared to stimulated cells expressing the Mock vector in the reference G allele. The results shown are from one representative experiment of 3 replicate pooled samples.

Following stimulation, none of the phosphorylated targets were detected in the rs10846744 risk C expressing cells, while all targets were significantly expressed in the rs10846744 reference G cells compared with the unstimulated condition p-CD79A (p=0.04), p-CD19 (p=0.04), p-Syk (p=0.005), p-Lyn (p=0.001), p-PLCγ2 (p=0.004) and p-PKCβ (p=0.003).

Overexpression or Silencing Of LAG3 Impacts Downstream Signaling Pathways

In order to directly assess the effect of LAG3 on downstream signaling pathways, we performed experiments wherein LAG3 was overexpressed in rs10846744 risk C expressing cells (which have decreased LAG3 levels) or silenced LAG3 in rs10846744 reference G expressing cells that express endogenous LAG-3 protein.

As shown in FIG. 10(B), overexpression of LAG3 in basal or stimulated rs10846744 risk C cells was associated with significantly increased levels of phosphorylated targets (p=0.04 for p-Lyn; p=0.03 for p-PKCβ in unstimulated cells and p=0.01 for p-Lyn; p=0.01 for p-PKCβ in stimulated cells) as compared with control cells (these being cells that were transfected with an empty vector). Silencing of LAG3 was associated with significantly lower levels of phosphorylated targets (p=0.002 for p-Lyn; p=0.009 for p-PKCβ in stimulated cells) in the rs10846744 reference G cells as compared with control cells (FIG. 8(C).

Carriers of the rs10846744 risk C allele had significantly less plasma soluble LAG3 (sLAG3). Given that LAG3 expression and function was reduced in the rs10846744 risk C expressing cells, we next determined if LAG3 protein levels would be significantly different in plasma isolated from HALP carriers of the reference G and risk C alleles; this study group constituting the discovery cohort.

Figure 11:
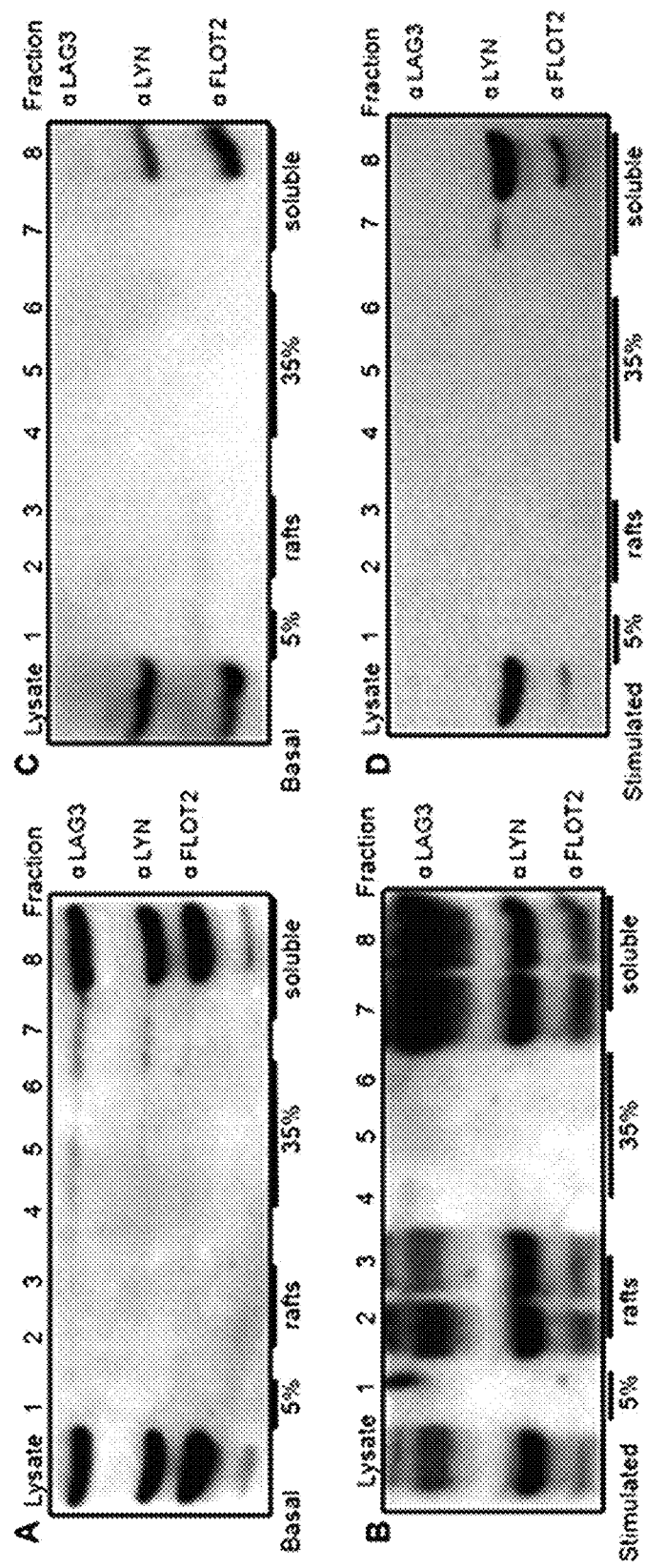
FIG. 11 illustrates how LAG3protein is a characteristic marker of lipid rafts.

FIG. 11 shows that the expression of LAG3 is reduced in lipid rafts and downstream signaling is impaired in rs10846744 risk C expressing cells. Since LAG3 has been shown to localize in lipid rafts in activated cells and affect downstream phosphosignaling, the inventor tested whether this LAG3 downregulation impacted downstream signaling pathways. In rs10846744 risk (CC) cells LAG3 was not identified in lipid rafts, whether cells were in the basal state or stimulated with PMA/ionomycin/IL-4. Lipid rafts were isolated from Epstein Barr Virus (EBV)-transformed B cells under basal or stimulated conditions (phorbol ester, PMA 500 ng/ml, ionomycin 250 ng/ml, and IL-4 100 U/ml) using a modified three-step sucrose density gradient for sodium carbonate-extracted homogenized lysates. Expression of the following targets was determined by immunoblotting using specific antibodies: LAG3; LYN and FLOT2 (Flotillin) (all lipid raft markers). Expression of LAG3 protein (normalized to FLOT2) localized to the lipid raft fractions of the stimulated reference (GG) cells (B, lanes 2-3) as compared with the basal condition (A, lanes 2-3), N=3, p=0.03. LAG3 protein was not detected in the risk (CC) cells whether under basal (C, lanes 2-3) or stimulated conditions (D, lanes 2-3). A two-sided Student's t-test was used to analyze results and the blot is representative of one of three independent experiments. P values less than 0.05 were considered significant.

As indicated above, FIG. 1 shows the plasma sLAG3 levels significantly associated with SCARB1 rs10846744. As seen in FIG. 1(A), plasma sLAG-3 levels were significantly lower in subjects homozygous for the risk C allele (CC: 3430±2339 pg/ml, n=22, p=0.03) as compared with subjects homozygous for the reference G allele (GG: 10,169±1120 pg/ml, n=96) or heterozygous subjects (GC: 11,139±2288 pg/ml, n=23).

Association of Rs10846744 and sLAG3 With Lipid Subfractions

The inventor next explored the association of rs10846744 and sLAG3 with lipid levels and HDL subfractions. In this HALP population, she did not observe an association of rs10846744 or sLAG-3 with total cholesterol, LDL-C, triglycerides, or HDL-C (data not shown). Likewise, we did not observe an association of rs10846744 or sLAG3 with plasma apolipoproteins (apoA-I, apoA-II, apoB, apoCI, apoCII, apoC-III, and apoE). A significant association of rs10846744 with HDL subfractions was observed when measured by NMR spectroscopy.

Referring again back to FIG. 2, the graph shows rs10846744 significantly associated with medium and small HDL particles as measured by NMR spectroscopy. The medium and small HDL particles were measured by NMR spectroscopy (Liposcience, Raleigh N.C.) in fasting plasma samples isolated from carriers homozygous for the reference G allele and homozygous for the risk C allele for rs10846744. The values shown are mean f standard deviation of medium and small HDL particles (μmol/L) and HDL size (nm).

Race/ethnicity, SCARB1 rs10846744 and other covariates are independent predictors of plasma LAG3 levels in MESA. In a multivariable regression model, race (p=0.0005), age (p=0.003), lipid medications (p=0.03), rs10846744 genotype (p=0.002), and smoking status (p<0.0001) were retained as independent predictors of plasma LAG3 levels (FIG. 5, Table 2.A). Plasma LAG-3 (p<0.007) remained an independent predictor of HDL-C levels even with adjustment by age (p=0.006), sex (p<0.0001), BMI (p<0.0001), TG (p<0.0001), alcohol use (p<0.0001), $Hgb_{A1c}$ (p=0.01), and systolic BP (p=0.03) (FIG. 5, Table 2.B).

Logistic multivariable regression analysis revealed that plasma LAG3 was not significantly associated with subclinical atherosclerosis (cIMT) (p=0.25) or coronary artery calcium score (CAC) (p=0.062). FIG. 12, Table 3 is a multivariable regression analysis showing the association of plasma LAG3 with CHD in MESA participants. Covariates included race, PCs of ancestry, age, study sites, sex, $Hgb_{A1c}$, BMI, lipid medications, lipids (TC and LDL-C), smoking pack years, systolic BP, and diastolic BP. The estimated coefficient of LAG3 (SE) was −0.078 (0.034). For LAG3, the odds ratio was estimated by comparing the $1^{st}$ quartile vs. $3^{rd}$ quartile of the variables. For the other continuous variables, the odds ratios were estimated by comparing $3^{rd}$ quartile vs. 1st quartile of the variables.*N=4707, *p<0.0001; **p=0.02; *p=0.0002; ++p=0.04; &p=0.002; &&p=0.03; ‖p=0.05

Logistic multivariable regression analysis revealed that, in addition to traditional risk factors such as age (p<0.0001), sex (p<0.0001), systolic blood pressure (p=0.0002), LDL-C (p=0.02), TC (p=0.04), lipid medications (p=0.002), Hgb$_{A1c}$ (p=0.03), and smoking (p=0.05), plasma LAG3 (beta −0.078, OR 1.15, p=0.02) was an independent predictor of CHD.

The prevalence of participants within the MESA cohort with HDL-C≥60 mg/dl was 26%, and within this group, the prevalence of CHD was 4% and not significant between the race/ethnic groups. HDL-C levels in subjects with CHD (n=55, 72.4±1.6 mg/dl) were not significantly different compared with subjects without CHD (n=1387, 71.8±0.3 mg/dl, p=0.71). However, plasma LAG3 levels were 2-fold lower in subjects with CHD (843.3±540.1 pg/m, n=55) as compared with subjects without CHD (1828±107.6 pg/ml, n=1386, p=0.04). In a logistic regression analysis, plasma LAG3 (beta −0.212, OR 1.45, p=0.004), age (p=0.006), sex (p=0.001), and diastolic blood pressure (p=0.03) were retained as independent predictors of CHD. FIG. 12, Table 4 is a regression analysis showing the association of plasma LAG3 with CHD in MESA participants with HDL-C≥60 mg/dl. Covariates included race, PCs of ancestry, age, study sites, sex, HgbA1c, BMI, lipid medications, lipids (TC and LDL-C), smoking pack years, systolic BP, and diastolic BP. The estimated coefficient of LAG3 (SE) was −0.212 (0.073). For LAG3, the odds ratio was estimated by comparing the 1st quartile vs. 3rd quartile of the variables. For the other continuous variables, the odds ratios were estimated by comparing 3rd quartile vs. 1st quartile of the variables. *N=1134, p=0.004; **p=0.006; +p=0.001; ++p=0.03 (Table 4).

The inventor also examined whether plasma LAG3 in the MESA cohort would significantly affect CHD risk prediction in comparison to the Framingham risk score. FIG. 12, Table 5 is a likelihood ratio test comparing model 2 (log-transformed plasma LAG3) with model 1 (Framingham Risk Score to estimate the 10-year cardiovascular risk of an individual). Table 5 indicates that inclusion of plasma LAG3 provided significant additional information in predicting CHD risk (p=0.039). Models 3 and 4 were adjusted for study sites, race, and PCs of ancestry; the likelihood ratio test of comparing model 4 with model 3 confirmed that inclusion of LAG3 provided significant additional information in predicting CHD risk (p=0.044). It can be seen in FIG. 12, Table 5, that plasma LAG3 increased CHD risk prediction in comparison to the Framingham risk score (p=0.039). When the model included adjustment for study sites, race, and PCs of ancestry, plasma LAG3 remained significant as a CHD risk predictor (p=0.04).

Given observance of a significant correlation between LAG3 and inflammatory markers from cultured B cells, the inventor investigated whether plasma LAG3 was associated with inflammatory markers available in the MESA datasets. FIG. 12, Table 6 shows the association of plasma LAG3 with inflammatory markers in MESA participants. Regression models were adjusted for age, sex, study site, race, and PCs of ancestry. All outcome variables and plasma LAG3 were log transformed. sTNFαR=soluble TNFα receptor; hs-CPR=high sensitive C reactive protein. As seen in Table 6, following multivariable regression analysis plasma LAG3 was positively associated with IL-10 (p<0.0001).

In conclusion, this establishes the utility of this novel strategy for qualitatively pre-screening a subject for one or more risk factors for developing cardiovascular disease, a second step of quantitatively detecting a LAG3 protein deficiency by either genotyping to pre-screen for presence of the SCARB rs10846744 and/or LAG3 rs870849 mutation or measuring plasma/serum LAG3 to identify patients with levels below 3400 pg/ml, followed by a tailored therapeutic regimen to mediating said diseases.

EXAMPLE 2

Materials and Methods

The culture medium used in all experiments was RPMI 1640 supplemented with 10% fetal bovine serum (FBS), 100 U/ml penicillin, 100 pg/ml streptomycin (all purchased from Life Technologies, Carlsbad, Calif.). For lymphocyte stimulation, phorbol 12-myristate acetate (PMA) and ionomycin calcium salt were purchased from Sigma-Aldrich (St. Louis, Mo.) while interleukin-4 (IL-4) was purchased from PeproTech (Oak Park, Calif.). LAG3 and isotype control fluorophore-conjugated monoclonal antibodies were purchased from Biolegend Inc. (San Diego, Calif.). Antibodies used for signaling were purchased from Cell Signaling Technologies (Beverly, Mass.): anti-CD79A (#3351), anti-phospho CD79A (Y182) (#5173), anti-CD19 (#3574), anti-phospho CD19 (Y531) (#3571), anti-Syk (#2712), anti-phospho-Syk (Y525/526) (#2710), anti-Lyn (#2796), anti-phospho Lyn (Y507) (#2731), anti-PLCγ2 (#3872), anti-phospho-PLCγ2 (Y759) (#3874), anti-phospho-PKCα/β II (T638/641) (#9375). Anti-PKCβ (Santa Cruz Biotechnology, Santa Cruz, Calif. sc-210) and anti-β-Actin (Sigma-Aldrich, St. Louis, Mo.) were purchased separately.

Lymphocytes isolated from HALP subjects were immortalized using Epstein Barr Virus to generate B lymphocytes (University of North Carolina Lineberger Comprehensive Cancer Center Tissue Culture Facility, Chapel Hill, N.C.). EBV transformed B lymphocytes were grown in suspension at density ~1-2×10$^6$ cells per ml of complete RPMI 1640 media with L-glutamine, supplemented with 10% FBS and 1% Penicillin-Streptomycin. The media was changed twice a week or more often as needed prior to using cells for experiments.

Total RNA was isolated from three HALP subjects homozygous for the reference G allele and three HALP subjects homozygous for the risk C allele and then subjected to full transcriptome sequencing using the Perkin Elmer next gen sequencing platform (RNA-Seq) (Perkin Elmer, Branford Conn.). Bioinformatics was performed using Perkin Elmer Gene Sifter software program. The data was adjusted by selecting total map reads, quality reads >20, log transformation, and using Benjamini Hochberg to correct for multiple testing. RNA targets of interest were validated by real-time PCR and western blotting using standard methodologies. RNA-Seq was performed on the separate six cell lines under conditions where cells were cultured in serum (usual culture conditions) and following stimulation with phorbol esters (PMA 500 ng/ml), ionomycin (250 ng/ml), and IL-4 (100 U/ml) for 6 h.

A number of assays were used to assess LAG3 expression and function in the six EBV-transformed B cell lines.

Flow cytometry: Flow cytometry was performed on a 10-laser flow cytometry (Becton Dickson, Franklin Lakes, N.J.). Dead cells were stained with Blue Dead Cell Stain Kit (Molecular Probes, Eugene, Oreg.). To measure the response of LAG3 in stimulated B cells we first modified and optimized a protocol previously published by Smeland et al (1). Cells were incubated with and without PMA (500 ng/ml), ionomycin (250 ng/ml) and IL-4 (100 U/ml) for varying time periods (0-4 h). Percent cell surface changes of cell surface LAG3 expression was calculated by using only the live cell fraction and then subtracting the percent isotype staining values from the percent staining values for cells treated with monoclonal LAG3 antibodies.

Cytokine secretion into the medium: Levels of interleukin 10 (IL-10) and Tumor Necrosis Factor α (TNFα) were measured in media aliquots isolated from cells cultured under basal and stimulated conditions for varying time periods (0-4 h) by multiplex (Milliplex; Millipore, Temecula, Calif.) on Luminex 200, using XMAP technology.

Western blotting: We used western blotting to measure total and phosphorylated expression of the following proteins known to be involved in downstream signaling in stimulated B cells: p-CD79A, p-CD19, p-Syk, p-Lyn, p-PLCγ2, and p-PKCβ. In some experiments we also stimulated cells with CD40 ligand (CD40L) (200 ng/mL) for 2 h and then isolated whole cell lysates for western blotting (FIGS. S4 and S5). Cells were solubilized with 50 mM Tris-HCl (pH 7.4), 1% NP-40, 0.25% Na deoxycholate, 150 mM NaCl, 1 mM PMSF, 5 mM NaF, 1 mM Na3VO4, 1 mM β-Glycerophosphate, 10 mM Na4P2O7, 2 mM EDTA and complete protease inhibitor cocktail (Roche Diagnostics Corp., San Francisco, Calif.). After 30 minutes of incubation on ice, lysates were clarified by centrifugation (10,000 g) for 15 minutes at 4° C. and supernatants were collected. Protein concentrations were determined using a BCA assay, and equal amounts were subjected to SDS/linear gradient PAGE following solubilization in Laemmli sample buffer. Gel-resolved proteins were subsequently electrotransferred to PVDF membranes via wet tank transfer, which were blocked with 5% nonfat milk prior to antibody incubation. Membranes were then incubated overnight at 4° C. first with antibodies to phospho-proteins, then total proteins. Antibody-antigen complexes were identified by chemiluminesence (ECL+System; Amersham Biosciences, Piscataway, N.J.). Anti-β-Actin was used as a loading control. Phospho-proteins were normalized to corresponding total proteins using Image Studio Lite 4.0 for quantification (Licor, Lincoln, Nebr.).

Lipid raft isolation. In order to assess expression of LAG3 in the plasma membrane lipid raft compartment, lipid raft membranes were isolated using 500 mM sodium carbonate (pH 11.0) and sucrose density centrifugation. The sucrose gradient method was performed essentially as described previously (2) with modifications. Cells ($1 \times 10^8$) were washed with ice-cold PBS and resuspended with 500 mM sodium carbonate, pH 11.0 (2) containing phosphatase and protease inhibitors (1 mM PMSF, 5 mM NaF, 1 mM Na3VO4, 1 mM β-Glycerophosphate, 10 mM Na4P2O7, 2 mM EDTA and Complete protease inhibitor cocktail (Roche Diagnostics Corp., San Francisco, Calif.). The solution was further homogenized with ten strokes in a Wheaton dounce homogenizer. For the discontinuous sucrose gradient, 300 μL of cleared supernatant was mixed with 300 μL of 85% sucrose and transferred to the bottom of a 2.2 mL Beckman centrifuge tube. The diluted lysate was overlaid with I ml 35% sucrose and finally 600 μL 5% sucrose. The samples were ultracentrifuged in a Beckman tabletop centrifuge at 70,000 g for 20 h at 4° C. Following centrifugation, gradients were portioned into 10, 220 μL fractions. Fractions 1-3 were pooled (combined fraction 1 on blot). To determine the location of lipid rafts and distinct proteins in the discontinuous sucrose gradient, 40 μL of the raft fractions (4 and 5 of the sucrose gradient, 2 and 3 on blot) and non-raft fractions were subjected to SDS-polyacrylamide gel electrophoresis and immunoblotted.

Overexpression and silencing of LAG3 assays. We used two experimental approaches to determine if the presence or absence of LAG3 was causal in altering downstream signaling pathways. We first overexpressed LAG3 in rs10846744 risk C expressing cells by transfecting them with lentiviral vectors expressing GFP tagged full-length human LAG3 cDNA. Our second approach was to use specific shRNA vectors to silence LAG3 expression in rs10846744 reference G expressing cells.

Lentiviral transfection and transduction: LAG3-GFP inserted into the pReceiver-Lv122 overexpressing vector, shRNA-LAG3 inserted into the psi-LVRH1MP RNAi silencing vector, scrambled shRNA, and lentiviral Mock GFP control vectors were obtained from GeneCopoeia (Rockville, Md.). Four shRNA to LAG3 were screened for selection of the plasmid with the most efficient knockdown. Lentivirus was generated by using Lenti-Pac HIV Expression Packaging Kit (GeneCopoeia, Rockville, Md.). Briefly, 2.5 μl of each individual lentiviral plasmid and 5.0 μl of EndoFectin Lenti reagent were added in Opti-MEM I, to form the DNA-EndoFectine complex. Twenty minutes after incubating the complex at room temperature, the DNA-EndoFectine complex was added to the dish with HEK 293 in DMEM with 10% FBS and incubated in 5% $CO_2$ at 37° C. overnight. The culture medium was replaced with fresh DMEM with 5% FBS and continued to be incubated. The viral-containing culture medium was collected 48 hr post transfection and concentrated after filtration. For transduction with lentivirus, $1 \times 10^6$ of EBV-transformed B lymphocytes in 1.5 ml of complete media were seeded in a 12-well plate and 500 μl of virus suspension was added. The cells were incubated at 37° C. for 72 h. To assess the effect of either overexpressing LAG3 in lymphocytes with the risk C allele or silencing LAG3 in lymphocytes with reference G allele on the downstream signaling pathway, transfected cells were stimulated with and without phorbol esters (500 ng/ml), ionomycin (250 ng/ml) and IL-4 (100 U/ml) cocktail for 2 hr and then processed for western blotting to assess phosphorylation of downstream signaling proteins.

Plasma or soluble lymphocyte activation gene 3 (sLAG3) assay. sLAG3 ELISA kits were purchased from RayBiotech, Inc. (Norcross Ga.) and sLAG3 was measured by first optimizing the kit. Aliquots of fasting plasma samples stored at −80° C. from 143 HALP subjects were thawed, diluted 3-fold, and then 100 μl were used for duplicates per sample for sLAG3 measurement. The standard curves were diluted 2-fold and yielded linearly associated data. Linear regressions were performed against the standard curve in order to quantify the plasma samples. Values are represented as the mean±standard error.

EXAMPLE 1

Mice

For all the atherosclerosis studies, we used 15 mice per group (30 per study) calculated from power calculations based on an expected 25% coefficient of variation of lesion area measurements, and 80% chance of detecting a 25% difference in lesion area. In all experiments, mice were fed a defined high cholesterol/high saturated fat diet for 10 weeks. Plasma lipid profiles were measured (LDL-C, HDL-C, triglycerides) both by standard colorometric assays, and by cholesterol determination in HPLC fractions. The amount of atherosclerotic lesion in the aortic roots and in the descending aorta were analyzed by established methods, including lesion volume assessed by lesion area of serial aortic root cross sections, and lesion area in en face Oil Red O-stained preparations of the aorta. Necrotic core size was measured as the area within lesions not stained by H&E. For each experimental group of mice, the numbers of CD4+, CD8+, and CD4+FoxP3+ T cells in the spleen and para-aortic lymph nodes were quantified and the activation phenotype of the T cells by flow cytometry (staining for CD62L, CD44, CD69, Lag-3 and PD-I) was determined.

Figure 13:
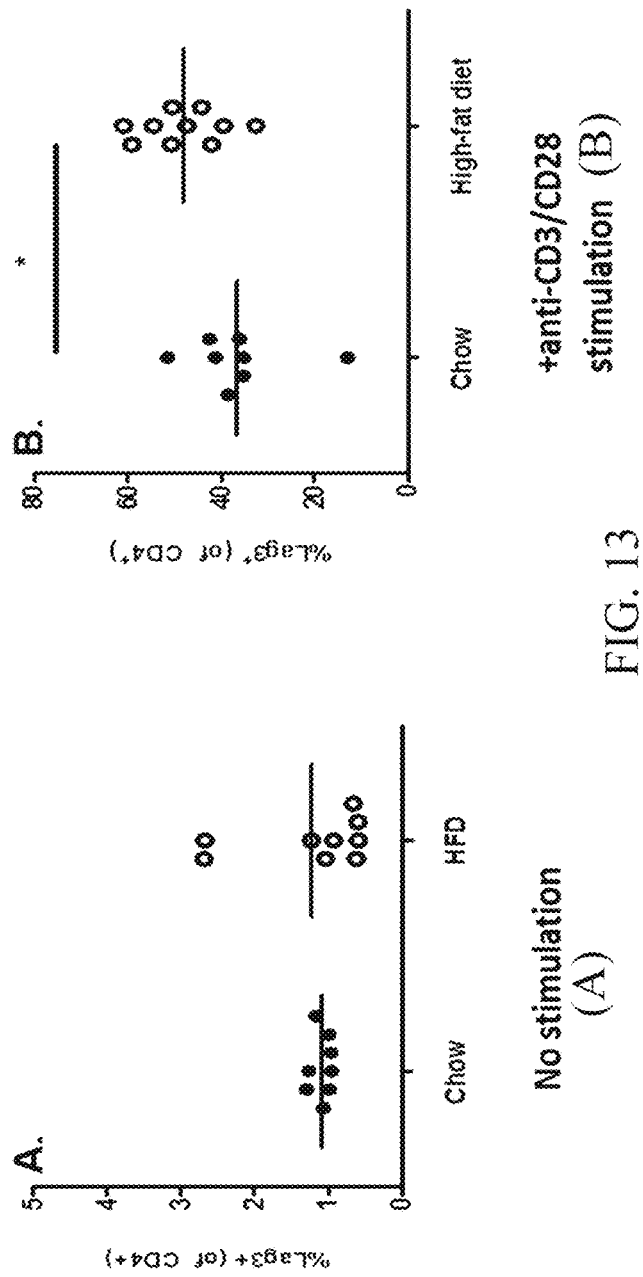
FIG. 13 is a composite figure ((A) and (B)) showing graphs of CD4+Lag3T cell activation in mice following high fat feeding.

When spleen cells were harvested from Idlr$^{-/-}$ mice after 10 weeks of chow vs. high fat diet and were stimulated ex vivo with anti-CD3/anti-CD28 for 24 h, 48.2±2.8% of CD4+ cells were Lag3+ compared to 36.7±3.9% Lag3+ cells from chow fed mice (31% increase, n=8-10, p<0.02). FIG. 13 is a graph of CD4+Lag3+ T cell activation in mice following high fat feeding. The graph indicates that a high fat diet resulted in activated CD4+ T cells.

Figure 14:
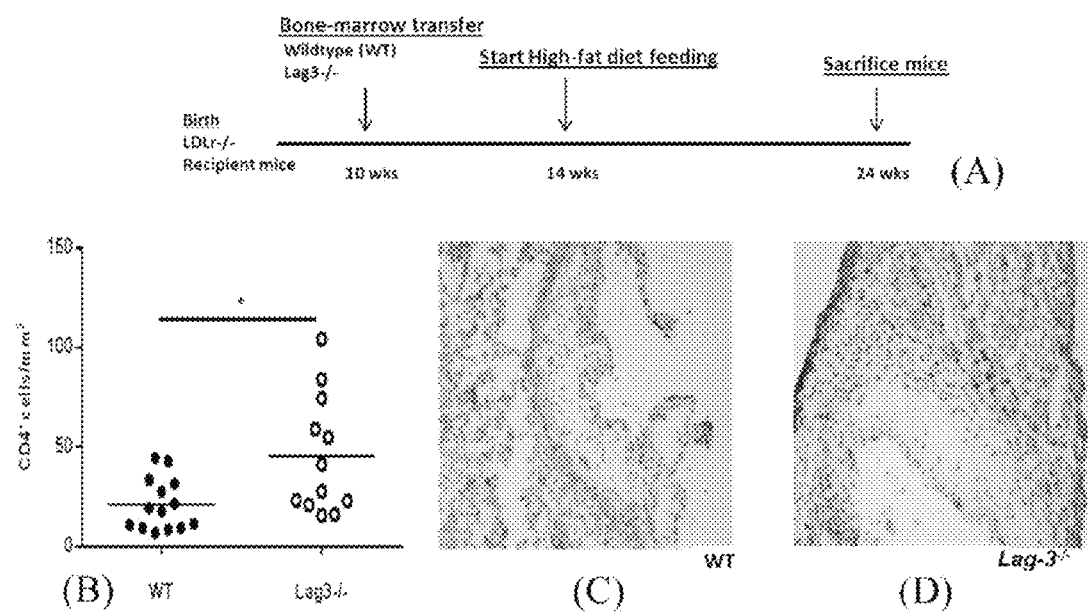
FIG. 14 is a composite figure ((A), (B), (C) and (D)) showing that bone marrow transfer Lag3null cells in Ldlr recipient mice and then fed a high fat diet led to significantly greater infiltration of $CD4^+T$ cells in the aortic root.

In order to examine the effect of bone marrow derived cells (BMDC) on atherosclerosis, we first transplanted either Lag3$^{-/-}$ or Lag3$^{+/+}$ BMDCs into 10 week old Ldlr$^{-/-}$ recipient mice that had been irradiated. These transplanted mice were allowed to equilibrate for 4 weeks prior to being fed a high fat/cholesterol diet for 10 weeks, and then sacrificed and analyzed for aortic lesion and immune parameters. There was a significant increase in aortic root lesional T cells in the Lag3$^{-/-}$ marrow recipients compared with controls (45.5±8.5 vs. 21.1±3.4 CD4+ cells/mm2 respectively, n=14 and 12, p=0.01, 2-fold increase) (FIG. 14). We also found significantly increased percentages of activated (CD62L-CD44+) CD4+ and CD8+ T cells in para-aortic lymph nodes in the Lag3$^{-/-}$ marrow recipients compared with controls (41.4±1.0 vs. 28.1±1.5 activated CD4+ cells, n=14, p<0.0001; 12.9±0.7 vs. 8.2±0.5 activated CD8+ cells; n=14, p<0.001). These results strongly support an anti-inflammatory, atheroprotective role for Lag-3 protein in the setting of hypercholesterolemia.

Figure 15:
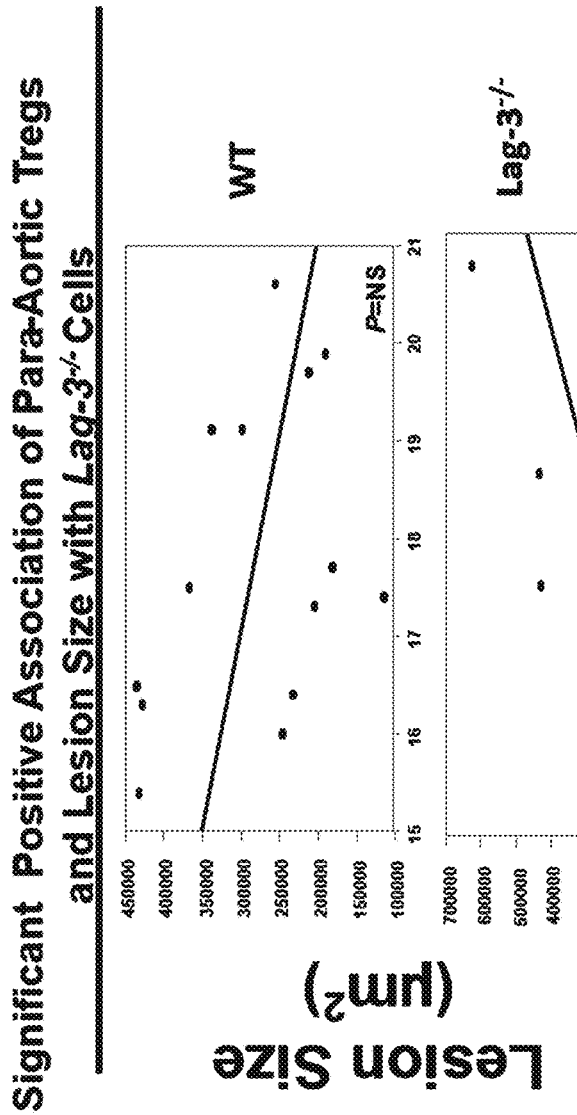
FIG. 15 is a composite figure ((A) and (B)) showing that bone marrow transfer of Lag3null cells in Ldlr recipient mice was significantly associated with increased atherosclerotic lesion size and increased percent of exTregs in draining para-aortic lymph nodes.

Tregs suppress pro-atherogenic T cell responses. See, Foks A C, Lichtman A H, Kuiper J. s.l., "Treating Atherosclerosis With Regulatory T Cells", Arterioscler Thromb Vasc Biol, vol. 35, pp. 280-287 (2015). However, the role of Lag-3 in this protective function is not known. Unexpectedly, the number of Tregs in the para-aortic lymph nodes positively correlated with lesion area in the Lag3[31] but not wild type marrow recipients (FIG. 15). This suggests that Lag-3 protein deficiency impairs Treg function but not expansion. It is noteworthy that a recent study showed selective deletion of CTLA-4 on FoxP3+ expressing cells resulted in expansion of FoxP3+ Tregs but these cells have impaired suppressive activity (termed exTregs). Since both CTLA-4 and Lag3 on Tregs may function to bind and block molecules on effector T cells (B7 and Class II MHC, respectively), it is likely that Lag3 deficient Tregs may also have defective suppressive activity.

Given the mechanism by which Lag3 inhibits CD4+ T cell responses, it was observed that Lag3 deficient mice showed significantly more lesional inflammation. It was observed expansion but lack of function of lymphoid Tregs in the setting of Lag3 protein deficiency, and a failure of adoptively transferred Lag3-deficient Tregs to control atherosclerosis relative to wild type Tregs.

Again, this established the novel strategy for using LAG3 expression profiling as a biomarker for assessing inflammasomes, chronic inflammatory diseases and dysfunctional HDL, followed by a tailored therapeutic regimen to mediating said diseases. Further utility is gained by a tailored therapeutic regimen of recombinant lymphocyte activation gene-3 as a companion therapeutic with an anti-hyperlipidemic and/or statin for atherosclerosis risk in human carriers of the SCARB1 and/or LAG3 variants or those identified with low plasma/serum LAG3 protein levels by other genetic or non-genetic causes.

EXAMPLE 2

Mice

Having identified that LAG3 deficiency in mice was significantly associated with altered Treg function and increased inflammatory cells in atherosclerotic mouse models, it was next determined if recombinant human soluble monomeric LAG3 would bind to mouse B cells that highly express its binding target MHC class II molecules. Mouse splenocytes (approx 1 million cells) from wildtype mouse were seeded to wells of a 96 well plate. Cells were spun down and resuspended in recombinant human soluble monomeric LAG3 solutions (0-162 µg protein/ml) in phosphate buffered saline (PBS) solution containing $Ca^{2+}/Mg^{2+}$. The experimental conditions were the following: Condition 1, 162 µg/ml (stock solution, Dilution factor 1); Condition 2, 32.4 µg/ml Dilution factor 5; Condition 3, 3.24 µg/ml Dilution factor 50; Condition 4, 0.32 µg/ml Dilution factor 500; Condition 5, 0 µg/ml. After a 30 min incubation, cells were spun down, washed once with FACS buffer (PBS with 0.5% bovine serum albumin, 0.05% sodium azide). 50 µl antibody cocktail was added containing Fc-block, anti-CD3 PerCP, anti-B220 FITC and LAG3/isotype control (anti-human LAG-3 and mouse IgG1 K isotype control APC, respectively). Cells were incubated at room temperature for 20 min and then added 150 µl FACS buffer. Cells were then washed with FACS buffer once more then finally resuspended in FACS buffer and analyzed by flow cytometry.

Figure 16:
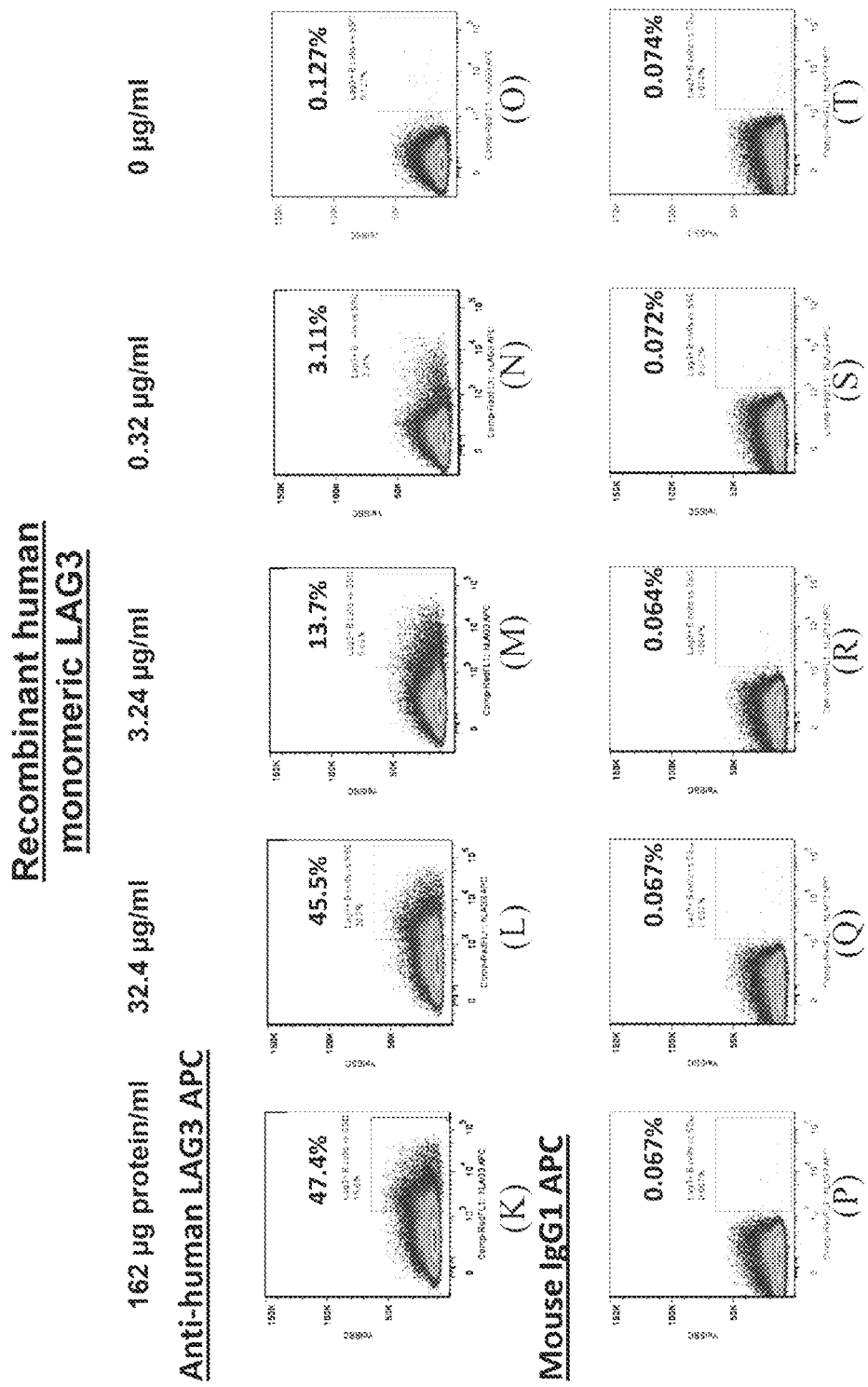
FIG. 16 is a composite graph ((A), (B),(C),(D),(E),(F), (G),(H),(I),(J) (K),(L),(M),(N),(O),(P),(Q),(R),(S),(T)) of recombinant human soluble monomeric LAG3 bound to mouse B splenocytes expressing MHC class II molecules in a dose-responsive manner.
Figure 17:
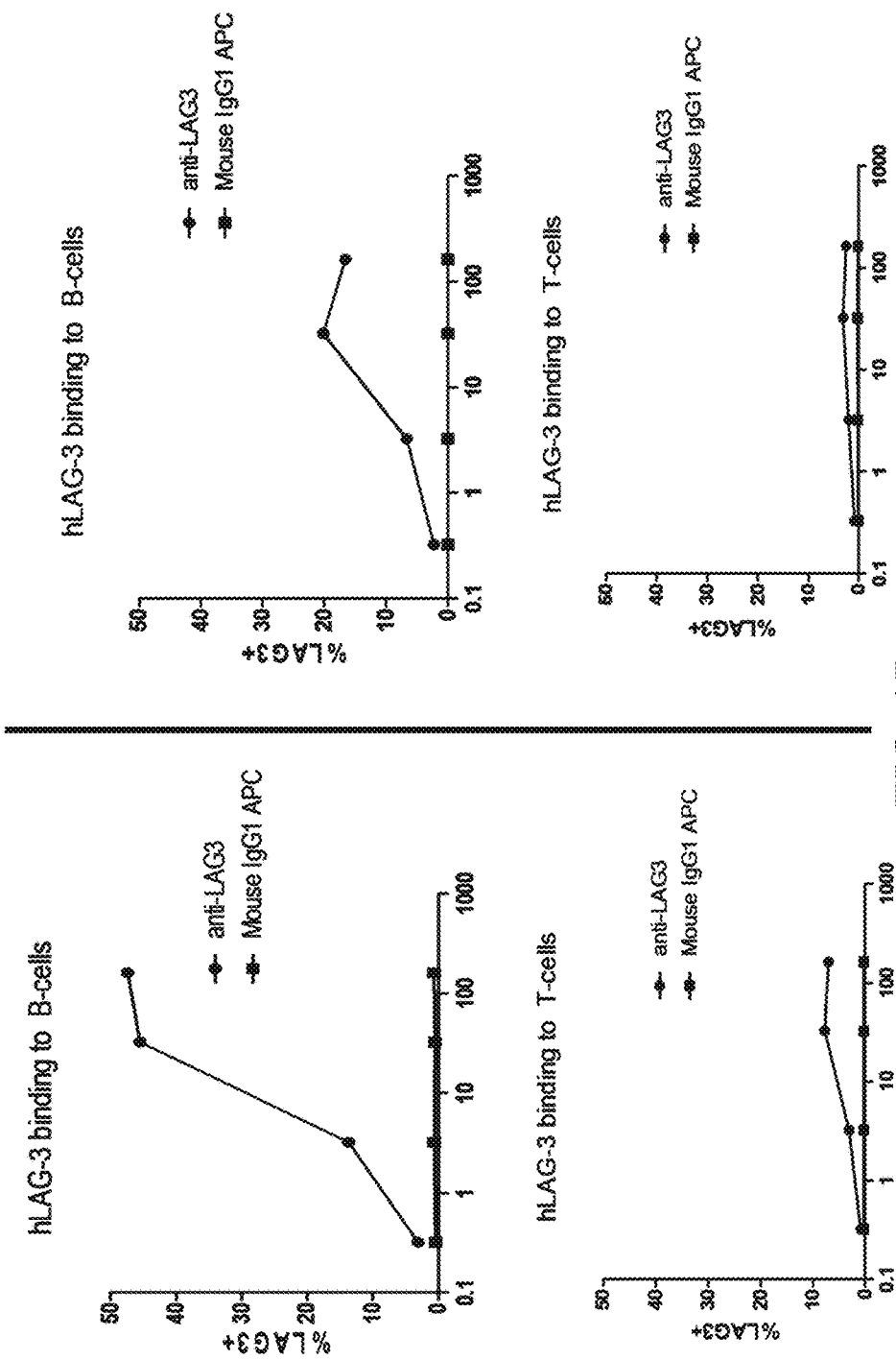
FIG. 17 is a graph showing recombinant human soluble monomeric LAG3bound preferentially to mouse B cells (which express MHC class II molecules) compared with mouse T cells (which do not express MHC class II molecules) in a dose-responsive manner.

As shown in FIG. 16 (first page), recombinant human soluble monomeric LAG3 bound to mouse B splenocytes expressing MHC class II molecules in a dose-responsive manner. In Figure 17 (second page), recombinant human soluble monomeric LAG-3 bound preferentially to mouse B cells (which express MHC class II molecules) compared with mouse T cells (which do not express MHC class II molecules) in a dose-responsive manner.

Figure 18:
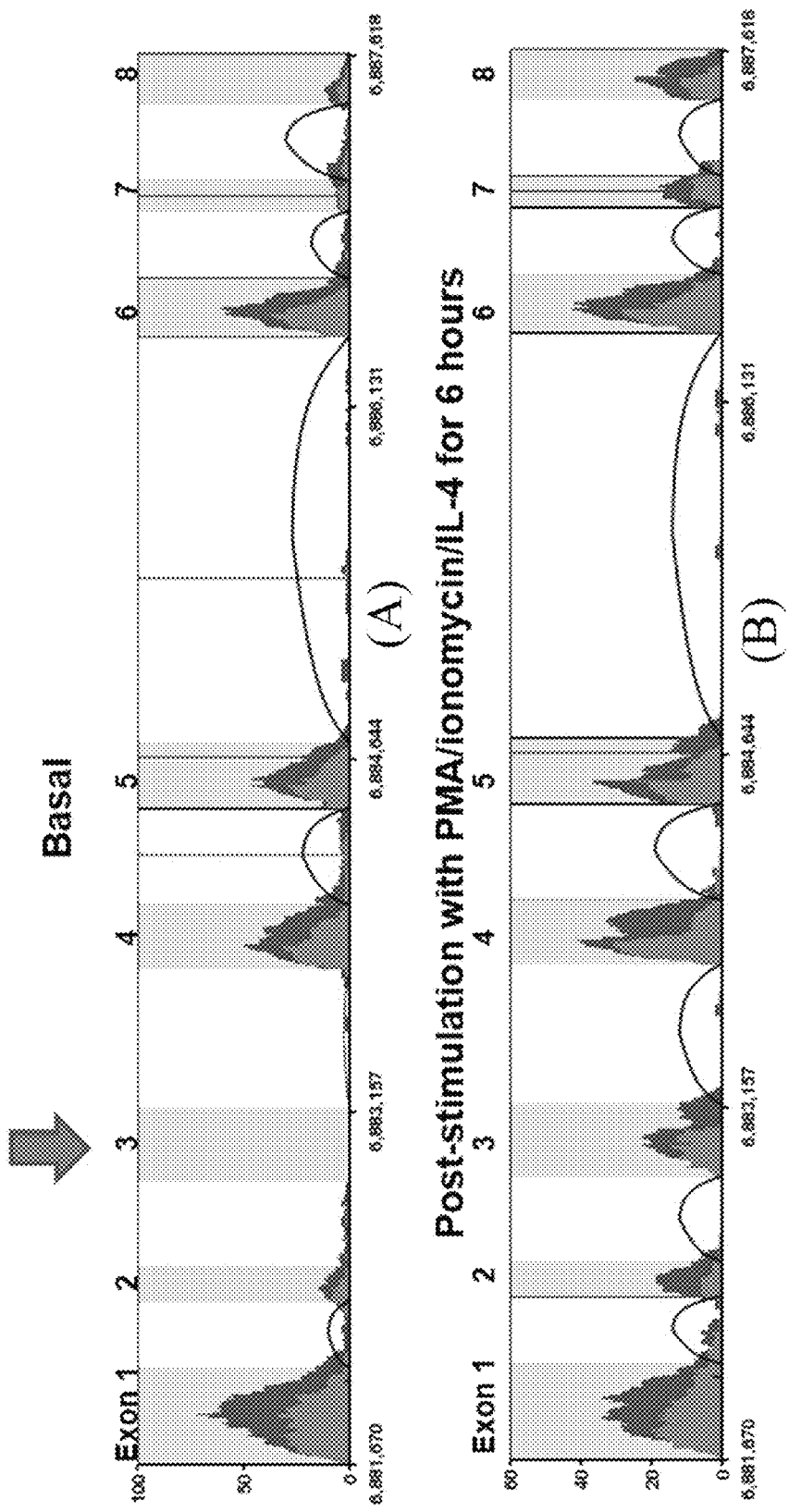
FIG. 18 is a composite figure ((A) and (B)) showing the differential expression of the LAG3 exon 3 transcript. The exon 3 is quiescent when cells are cultured under routine tissue culture conditions, but the exon 3 transcript increases when cells are stimulated with agents such phorbol esters, ionomycin, and interleukin-4.

FIG. 18 illustrates the differential expression of the LAG3 exon 3 transcript in lymphocytes under basal and post-stimulation conditions. The inventor uniquely identified that the exon 3 of the LAG3 gene is differentially expressed between human B lymphocytes cultured under basal or quiescent conditions compared with cells stimulated with phorbol ester, ionomycin, and IL-4. Exon 3 transcription is essential to translate into the extra loop of domain 1 of the LAG3 protein that binds to MHC class II molecules.

LAG-3 Transcriptional Regulation.

The LAG-3 protein structure consists of four Ig-like ectodomains, a connecting peptide, transmembrane and cytoplasmic domain. The LAG3 protein structure is similar to that of CD4 although the amino acid sequence homology is only 20%. Creg J. Workman, Dario A. A. Vignali, "The CD4-Related Molecule, LAG-3 (CD223), Regulates the Expansion of Activated T Cells, Eur. Jl. of Immunology, 24 Mar. (2003). In comparison to CD4, LAG3 protein uniquely contains an extra loop of 30 amino acids as part of domain 1. This extra loop is encoded in exon 3 and it is this loop that has been shown to bind to the MHC class II receptors. Huard et al., Characterization Of The Major Histocompatibility Complex Class II Binding Site On LAG-3 Protein, Proc Natl Acad Sci USA., 94(11): 5744-5749 (May 1997).

In FIG. 18 it is demonstrated that exon 3 transcription is diminished, if absent, in basal quiescent cells and increased when cells were stimulated with a cocktail containing phorbol ester (PMA)/ionomycin/IL-4. In pondering this novel observation, it makes sense that the extra loop needs to be transcribed only when cells are activated. An embodiment of recombinant human LAG3 can also be an agent that mimics activation of LAG3 exon 3 (LAG3 mimetic) in order to increase RNA and protein expression of the extra loop which binds MHC class II molecules. Mimetics of LAG3 exon 3 activation can include molecules and/or agents that affect the formation of alternate DNA or RNA structures that affect RNA transcription, including molecules that affect intracellular or extracellular cations that affect alternate DNA or RNA structures such as potassium, sodium, lithium or calcium. Mimetics of LAG3 exon 3 activation can include molecules and/or agents that affect alternative splicing that would include or exclude transcription of the LAG3 exon 3.

Having now fully set forth the preferred embodiment, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A method for treating chronic inflammatory and cardiovascular disease in a human adult subject, comprising the steps of:
   performing a qualitative pre-screen of said subject by symptotic analysis to detect a LAG3 deficiency marker indicative of a potential deficiency of LAG3 protein;
   performing a quantitative test on said subject to confirm said LAG3 protein deficiency by one of genotyping or measuring plasma/serum LAG3;
   administering a therapeutic regimen to said subject having a confirmed LAG3 protein deficiency comprising a combination of hLAG3-Ig as an adjuvant with at least one chemotherapeutic agent.

2. The method of claim 1, wherein said step of performing a qualitative pre-screen of said subject comprises pre-screening a medical record for a LAG3 deficiency marker.

3. The method of claim 1, wherein said step of performing a qualitative pre-screen of said subject comprises performing pre-screening a family history for a LAG-deficiency marker.

4. The method of claim 1, wherein said step of performing a quantitative test comprises performing a quantitative test on a blood sample from said subject to confirm said LAG3 protein deficiency.

5. The method of claim 4, wherein said step of performing a quantitative test on said blood sample comprises performing an assay.

6. The method of claim 4, wherein said step of performing a quantitative test on said blood sample comprises performing a genetic test.

7. The method of claim 1, wherein said step of performing a quantitative test comprises performing both a genetic test and an assay of a plasma sample from said subject for presence of low level expression of LAG3.

8. The method of claim 6, wherein said step of performing a quantitative genetic test comprises performing a quantitative genetic test that is configured to detect a polymorphism in the coding sequence of the SCARB1 or LAG3 genes.

9. The method of claim 8, wherein said polymorphism is a SCARB1 rs10846744 or LAG3 rs870849 mutation.

10. The method of claim 8, wherein said step of performing a quantitative test on said blood sample includes amplifying at least a portion of a SCARB1 or LAG3 gene prior to identifying the allelic variant.

11. The method of claim 5, wherein said step of performing an assay further comprises performing an assay that is configured to measure low LAG3 below 3400 pg/ml.

12. The method of claim 11, wherein said step of performing an assay further comprises performing an ELISA assay.

13. The method of claim 1, wherein said step of administering a therapeutic regimen to said subject comprises administering recombinant human LAG3 by periodic administration.

14. The method of claim 1, wherein said step of administering a therapeutic regimen to said subject comprises administering recombinant a LAG3 mimetic by periodic administration.

15. The method of claim 13, wherein said step of administering a therapeutic regimen to said subject comprising administering the chemotherapeutic agent probucol.

16. The method of claim 15, wherein said step of administering probucol comprises periodic administration within a range of from three to four months.

17. The method of claim 15, wherein said step of administering probucol comprises periodic administration for a remainder of said subject's lifetime.

18. The method of claim 13, wherein said step of administering recombinant human LAG3 by periodic administration comprises administering Human LAG3 protein.

19. The method of claim 1, wherein said chemotherapeutic agent comprises any one or more agents selected from the group consisting of an anti-inflammatory agent, an agent that improves HDL-C function, size, and/or composition in the subject, an agent that decreases dysfunctional HDL-C in the subject, a PCSK9 inhibitors, and a LAG3 mimetic.

20. The method of claim 1, further comprising a step of monitoring said subject during said periodic administration to determine effect on LDL oxidation and plasma-HDL cholesterol and plasma/serum cytokines.

21. The method of claim 20, wherein said step of monitoring comprises performing monthly safety labs with comprehensive profiles and EKGs.

22. A method for treating chronic inflammatory and cardiovascular disease in a human adult subject, comprising the steps of:
   performing a qualitative pre-screen of said subject by symptotic analysis to detect a LAG3 deficiency marker indicative of a potential deficiency of LAG3 protein;
   performing a quantitative test on said subject by one of genotyping or measuring plasma/serum LAG3 to confirm said LAG3 protein deficiency;
   administering a therapeutic regimen of hLAG3-Ig to a subject having a confirmed LAG3 protein deficiency.

23. The method of claim 22, wherein said step of performing a qualitative pre-screen of said subject comprises pre-screening a medical record for a LAG3 deficiency marker.

24. The method of claim 22, wherein said step of performing a qualitative pre-screen of said subject comprises pre-screening a family history for a LAG-deficiency marker.

25. The method of claim 22, wherein said step of performing a quantitative test comprises administering a quantitative test on a blood sample from said subject to confirm said LAG3 protein deficiency.

26. The method of claim 25, wherein said step of performing a quantitative test on said blood sample comprises performing an assay.

27. The method of claim 25, wherein said step of performing a quantitative test on said blood sample comprises performing a genetic test.

28. The method of claim 27, wherein said step of performing a quantitative test comprises performing both a genetic test and an assay of a plasma sample from said subject for presence of low level expression of LAG3.

29. The method of claim 25, wherein said step of performing a quantitative genetic test comprises performing a quantitative genetic test that is configured to detect a polymorphism in the coding sequence of the SCARB1 or LAG3 genes, and said polymorphism is a SCARB1 rs10846744 or LAG3 rs870849 mutation.

30. The method of claim 22, further comprising a step of administering an antigen, and wherein said step of administering a therapeutic regimen of hLAG3-Ig comprises administering hLAG3-Ig as an adjuvant to said antigen.

31. The method of claim 30, wherein said wherein said step of administering an antigen comprises administering an antigen configured for lowering HDL cholesterol levels and as antioxidants.

32. The method of claim 31, wherein said step of administering an antigen comprises administering probucol.

33. The method of claim 24, further comprising a step of monitoring said human adult subject by conducting monthly safety labs with comprehensive profiles and EKGs.

* * * * *

SEQUENCE LISTING

```
<160> NUMBER OF SEQ ID NOS: 2

<210> SEQ ID NO 1
<211> LENGTH: 521
<212> TYPE: PRT
<213> ORGANISM: Mus musculus
<220> FEATURE:
<221> NAME/KEY: SOURCE
<222> LOCATION: (1)..(521)
<223> OTHER INFORMATION: organism="Mus musculus", strain="C57BL/6",
      db_xref="taxon:10090", chromosome="6", map="6"
<220> FEATURE:
<221> NAME/KEY: SIG_PEPTIDE
<222> LOCATION: (1)..(22)
<223> OTHER INFORMATION: Potential; propagated from UniProtKB/Swiss-Prot
      (Q61790.1) calculated_mol_wt=2485
<220> FEATURE:
<221> NAME/KEY: PROTEIN
<222> LOCATION: (1)..(521)
<223> OTHER INFORMATION: product="lymphocyte activation gene 3 protein
      precursor"; note="lymphocyte activation gene 3 protein"
<220> FEATURE:
<221> NAME/KEY: mat_peptide
<222> LOCATION: (23)..(521)
<223> OTHER INFORMATION: propagated from UniProtKB/Swiss-Prot
      (Q61790.1); calculated_mol_wt=54511
<220> FEATURE:
<221> NAME/KEY: MISC_FEATURE
<222> LOCATION: (168)..(246)
<223> OTHER INFORMATION: Immunoglobulin domain; pfam00047
<220> FEATURE:
<221> NAME/KEY: MISC_FEATURE
<222> LOCATION: (181)..(253)
<223> OTHER INFORMATION: Immunoglobulin like; smart00410
<220> FEATURE:
<221> NAME/KEY: MISC_FEATURE
<222> LOCATION: (261)..(344)
<223> OTHER INFORMATION: Immunoglobulin like; smart00410
<220> FEATURE:
<221> NAME/KEY: MISC_FEATURE
<222> LOCATION: (261)..(344)
<223> OTHER INFORMATION: Immunoglobulin domain; cl11960
<220> FEATURE:
<221> NAME/KEY: MISC_FEATURE
<222> LOCATION: (443)..(463)
<223> OTHER INFORMATION: site_type="transmembrane region"; propagated
      from UniProtKB/Swiss-Prot (Q61790.1)
<220> FEATURE:
<221> NAME/KEY: MISC_FEATURE
<222> LOCATION: (493)..(518)
<223> OTHER INFORMATION: region_name="13 X 2 AA tandem repeats of E-X";
      propagated from UniProtKB/Swiss-Prot (Q61790.1)
```

```
<300> PUBLICATION INFORMATION:
<301> AUTHORS: Gagliani N, Magnani CF, Huber S, Gianolini ME, Pala M,
      Licona-Limon P, Guo B, Herbert DR, Bulfone A, Trentini F, Di
      Serio C, Bacchetta R, Andreani M, Brockmann L, Gregori S, Flavell
      RA and Roncarolo MG.
<302> TITLE: Coexpression of CD49b and LAG-3 identifies human and mouse
      T Coexpression of CD49b and LAG-3 identifies human and mouse T
<303> JOURNAL: Nature Medicine
<304> VOLUME: 19
<305> ISSUE: 6
<306> PAGES: 739-746
<307> DATE: 2013
<313> RELEVANT RESIDUES IN SEQ ID NO: (1)..(521)
<300> PUBLICATION INFORMATION:
<301> AUTHORS: Woo SR, Turnis ME, Goldberg MV, Bankoti J, Selby M,
      Nirschl CJ, Bettini ML, Gravano DM, Vogel P, Liu CL,
      Tangsombatvisit S, Grosso JF, Netto G, Smeltzer MP, Chaux A,
      Utz PJ, Workman CJ, Pardoll DM, Korman AJ, Drake CG and
      Vignali DA.
<302> TITLE: Immune inhibitory molecules LAG-3 and PD-1 synergistically
      regulate T-cell function to promote tumoral immune escape
<303> JOURNAL: Cancer Research
<304> VOLUME: 72
<305> ISSUE: 4
<306> PAGES: 917-927
<307> DATE: 2012
<313> RELEVANT RESIDUES IN SEQ ID NO: (1)..(521)
<300> PUBLICATION INFORMATION:
<301> AUTHORS: Butler NS, Moebius J, Pewe LL, Traore B, Doumbo OK,
      Tygrett LT, Waldschmidt TJ, Crompton PD and Harty JT.
<302> TITLE: Therapeutic blockade of PD-L1 and LAG-3 rapidly clears
      established blood-stage Plasmodium infection
<303> JOURNAL: Nat. Immunol.
<304> VOLUME: 13
<305> ISSUE: 2
<306> PAGES: 188-195
<307> DATE: 2012
<313> RELEVANT RESIDUES IN SEQ ID NO: (1)..(521)
<300> PUBLICATION INFORMATION:
<301> AUTHORS: Bettini M, Szymczak-Workman AL, Forbes K, Castellaw AH,
      Selby M, Pan X, Drake CG, Korman AJ and Vignali DA.
<302> TITLE: Cutting edge: accelerated autoimmune diabetes in the
      absence of LAG-3
<303> JOURNAL: Journal of Immunology
<304> VOLUME: 187
<305> ISSUE: 7
<306> PAGES: 3493-3498
<307> DATE: 2011
<313> RELEVANT RESIDUES IN SEQ ID NO: (1)..(521)
<300> PUBLICATION INFORMATION:
<301> AUTHORS: Lucas CL, Workman CJ, Beyaz S, LoCascio S, Zhao G,
      Vignali DA and Sykes M.
<302> TITLE: LAG-3, TGF-beta, and cell-intrinsic PD-1 inhibitory
      pathways contribute to CD8 but not CD4 T-cell tolerance induced by
      allogeneic BMT with anti-CD40L
<303> JOURNAL: Blood
<304> VOLUME: 117
<305> ISSUE: 20
<306> PAGES: 5532-5540
<307> DATE: 2011
<313> RELEVANT RESIDUES IN SEQ ID NO: (1)..(521)
<300> PUBLICATION INFORMATION:
<301> AUTHORS: Workman CJ, Rice DS, Dugger KJ, Kurschner C and
      Vignali DA.
<302> TITLE: Phenotypic analysis of the murine CD4-related glycoprotein,
      CD223 (LAG-3)
<303> JOURNAL: Eur. J. Immunol.
<304> VOLUME: 32
<305> ISSUE: 8
<306> PAGES: 2255-2263
<307> DATE: 2002
<313> RELEVANT RESIDUES IN SEQ ID NO: (1)..(521)
<300> PUBLICATION INFORMATION:
<301> AUTHORS: Huard B, Mastrangeli R, Prigent P, Bruniquel D, Donini S,
      El-Tayar N, Maigret B, Dreano M and Triebel F.
<302> TITLE: Characterization of the major histocompatibility complex
      class II binding site on LAG-3 protein
```

```
<303> JOURNAL: Proc. Natl. Acad. Sci. U.S.A.
<304> VOLUME: 94
<305> ISSUE: 11
<306> PAGES: 2744-5749
<307> DATE: 1997
<313> RELEVANT RESIDUES IN SEQ ID NO: (1)..(521)
<300> PUBLICATION INFORMATION:
<301> AUTHORS: Mastrangeli R, Micangeli E and Donini S.
<302> TITLE: Cloning of murine LAG-3 by magnetic bead bound homologous
       probes and PCR (gene-capture PCR)
<303> JOURNAL: Anal. Biochem.
<304> VOLUME: 241
<305> ISSUE: 1
<306> PAGES: 93-102
<307> DATE: 1996
<313> RELEVANT RESIDUES IN SEQ ID NO: (1)..(521)
<300> PUBLICATION INFORMATION:
<301> AUTHORS: Miyazaki T, Dierich A, Benoist C and Mathis D..
<302> TITLE: LAG-3 is not responsible for selecting T helper cells in
       CD4-deficient mice
<303> JOURNAL: Int. Immunol.
<304> VOLUME: 8
<305> ISSUE: 5
<306> PAGES: 725-729
<307> DATE: 1996
<313> RELEVANT RESIDUES IN SEQ ID NO: (1)..(521)
<300> PUBLICATION INFORMATION:
<301> AUTHORS: Miyazaki T, Dierich A, Benoist C and Mathis D.
<302> TITLE: Independent modes of natural killing distinguished in mice
       lacking lag-3
<303> JOURNAL: Science
<304> VOLUME: 2722
<305> ISSUE: 5260
<306> PAGES: 405-408
<307> DATE: 1996
<313> RELEVANT RESIDUES IN SEQ ID NO: (1)..(521)

<400> SEQUENCE: 1

Met Arg Glu Asp Leu Leu Leu Gly Phe Leu Leu Leu Gly Leu Leu Trp
        -20                 -15                 -10

Glu Ala Pro Val Val Ser Ser Gly Pro Gly Lys Glu Leu Pro Val Val
     -5              -1   1               5                  10

Trp Ala Gln Glu Gly Ala Pro Val His Leu Pro Cys Ser Leu Lys Ser
                 15                  20                  25

Pro Asn Leu Asp Pro Asn Phe Leu Arg Arg Gly Gly Val Ile Trp Gln
             30                  35                  40

His Gln Pro Asp Ser Gly Gln Pro Thr Pro Ile Pro Ala Leu Asp Leu
             45                  50                  55

His Gln Gly Met Pro Ser Pro Arg Gln Pro Ala Pro Gly Arg Tyr Thr
             60                  65                  70

Val Leu Ser Val Ala Pro Gly Gly Leu Arg Ser Gly Arg Gln Pro Leu
75                  80                  85                  90

His Pro His Val Gln Leu Glu Glu Arg Gly Leu Gln Arg Gly Asp Phe
                 95                 100                 105

Ser Leu Trp Leu Arg Pro Ala Leu Arg Thr Asp Ala Gly Glu Tyr His
            110                 115                 120

Ala Thr Val Arg Leu Pro Asn Arg Ala Leu Ser Cys Ser Leu Arg Leu
            125                 130                 135

Arg Val Gly Gln Ala Ser Met Ile Ala Ser Pro Ser Gly Val Leu Lys
            140                 145                 150

Leu Ser Asp Trp Val Leu Leu Asn Cys Ser Phe Ser Arg Pro Asp Arg
155                 160                 165                 170

Pro Val Ser Val His Trp Phe Gln Gly Gln Asn Arg Val Pro Val Tyr
                175                 180                 185
```

```
Asn Ser Pro Arg His Phe Leu Ala Glu Thr Phe Leu Leu Pro Gln
            190                 195                 200

Val Ser Pro Leu Asp Ser Gly Thr Trp Gly Cys Val Leu Thr Tyr Arg
            205                 210                 215

Asp Gly Phe Asn Val Ser Ile Thr Tyr Asn Leu Lys Val Leu Gly Leu
            220                 225                 230

Glu Pro Val Ala Pro Leu Thr Val Tyr Ala Ala Glu Gly Ser Arg Val
235                 240                 245                 250

Glu Leu Pro Cys His Leu Pro Pro Gly Val Gly Thr Pro Ser Leu Leu
                255                 260                 265

Ile Ala Lys Trp Thr Pro Pro Gly Gly Gly Pro Glu Leu Pro Val Ala
            270                 275                 280

Gly Lys Ser Gly Asn Phe Thr Leu His Leu Glu Ala Val Gly Leu Ala
            285                 290                 295

Gln Ala Gly Thr Tyr Thr Cys Ser Ile His Leu Gln Gly Gln Gln Leu
            300                 305                 310

Asn Ala Thr Val Thr Leu Ala Val Ile Thr Val Thr Pro Lys Ser Phe
315                 320                 325                 330

Gly Leu Pro Gly Ser Arg Gly Lys Leu Leu Cys Glu Val Thr Pro Ala
                335                 340                 345

Ser Gly Lys Glu Arg Phe Val Trp Arg Pro Leu Asn Asn Leu Ser Arg
            350                 355                 360

Ser Cys Pro Gly Pro Val Leu Glu Ile Gln Glu Ala Arg Leu Leu Ala
            365                 370                 375

Glu Arg Trp Gln Cys Gln Leu Tyr Glu Gly Gln Arg Leu Leu Gly Ala
380                 385                 390

Thr Val Tyr Ala Ala Glu Ser Ser Ser Gly Ala His Ser Ala Arg Arg
395                 400                 405                 410

Ile Ser Gly Asp Leu Lys Gly Gly His Leu Val Leu Val Leu Ile Leu
                415                 420                 425

Gly Ala Leu Ser Leu Phe Leu Leu Val Ala Gly Ala Phe Gly Phe His
            430                 435                 440

Trp Trp Arg Lys Gln Leu Leu Leu Arg Arg Phe Ser Ala Leu Glu His
            445                 450                 455

Gly Ile Gln Pro Phe Pro Ala Gln Arg Lys Ile Glu Glu Leu Glu Arg
460                 465                 470

Glu Leu Glu Thr Glu Met Gly Gln Glu Pro Glu Pro Glu Pro Glu Pro
475                 480                 485                 490

Gln Leu Glu Pro Glu Pro Arg Gln Leu
                495

<210> SEQ ID NO 2
<211> LENGTH: 525
<212> TYPE: PRT
<213> ORGANISM: Homo sapiens
<220> FEATURE:
<221> NAME/KEY: SOURCE
<222> LOCATION: (1)..(525)
<223> OTHER INFORMATION: organism="Homo sapiens"; db_xref="taxon:9606";
      chromosome="12"; map="12p13.31"
<220> FEATURE:
<221> NAME/KEY: PROTEIN
<222> LOCATION: (1)..(525)
<223> OTHER INFORMATION: /product="lymphocyte activation gene 3 protein
      precursor" /note="lymphocyte activation gene 3 protein;
      lymphocyte-activation gene 3"
<220> FEATURE:
<221> NAME/KEY: SIG_PEPTIDE
<222> LOCATION: (1)..(22)
```

```
<223> OTHER INFORMATION: inference="COORDINATES: ab initio prediction:
      SignalP:4.0"; calculated_mol_wt=2584
<220> FEATURE:
<221> NAME/KEY: mat_peptide
<222> LOCATION: (23)..(525)
<223> OTHER INFORMATION: product="lymphocyte activation gene 3 protein";
      calculated_mol_wt=54883
<220> FEATURE:
<221> NAME/KEY: MISC_FEATURE
<222> LOCATION: (174)..(259)
<223> OTHER INFORMATION: region_name="Ig_2"; note="Immunoglobulin
      domain; pfam13895"; db_xref="CDD:290606"
<220> FEATURE:
<221> NAME/KEY: MISC_FEATURE
<222> LOCATION: (185)..(259)
<223> OTHER INFORMATION: region_name="IG_like"; note="Immunoglobulin
      like; smart00410"; db_xref="CDD:214653"
<220> FEATURE:
<221> NAME/KEY: MISC_FEATURE
<222> LOCATION: (263)..(336)
<223> OTHER INFORMATION: region_name="Ig"; note="Immunoglobulin domain;
      cl11960"; db_xref="CDD:299845"
<220> FEATURE:
<221> NAME/KEY: MISC_FEATURE
<222> LOCATION: (267)..(348)
<223> OTHER INFORMATION: region_name="IG_like"; note="Immunoglobulin
      like; smart00410"; db_xref="CDD:214653"
<220> FEATURE:
<221> NAME/KEY: SITE
<222> LOCATION: (451)..(471)
<223> OTHER INFORMATION: site_type="transmembrane region";
      note="propagated from UniProtKB/Swiss-Prot (P18627.5)"
<220> FEATURE:
<221> NAME/KEY: MISC_FEATURE
<222> LOCATION: (501)..(524)
<223> OTHER INFORMATION: region_name="12 X 2 AA tandem repeats of E-X";
      note="propagated from UniProtKB/Swiss-Prot (P18627.5)"
<300> PUBLICATION INFORMATION:
<301> AUTHORS: Ma C, Lu Z, Wang K, Bie L and Shen Q.
<302> TITLE: [Elevated expression of lymphocyte activation gene-3 on
      peripheral Blood CD8(+) T lymphocytes in patients with chronic
      hepatitis B virus infection]
<303> JOURNAL: Xi Bao Yu Fen Zi Mian Yi Xue Za Zhi
<304> VOLUME: 32
<305> ISSUE: 4
<306> PAGES: 532-537
<307> DATE: 2016-01-01
<313> RELEVANT RESIDUES IN SEQ ID NO: (1)..(525)
<300> PUBLICATION INFORMATION:
<301> AUTHORS: Zeng H, Liu Y, Guo W, Wang X and Chen L.
<302> TITLE: [Decreased expression levels of LAG-3 and CD49b on CD14+
      cells In peripheral blood of patients with recurrent spontaneous
      abortion]
<303> JOURNAL: Xi Bao Yu Fen Zi Mian Yi Xue Za Zhi
<304> VOLUME: 32
<305> ISSUE: 3
<306> PAGES: 369-372
<307> DATE: 2016-01-01
<313> RELEVANT RESIDUES IN SEQ ID NO: (1)..(525)
<300> PUBLICATION INFORMATION:
<301> AUTHORS: Do JS, Visperas A, Sanogo YO, Bechtel JJ, Dvorina N,
      Kim S, Jang E, Stohlman SA, Shen B, Fairchild RL, Baldwin Iii WM,
      Vignali DA and Min B.
<302> TITLE: An IL-27/Lag3 axis enhances Foxp3+ regulatory T
      cell-suppressive function and therapeutic efficacy
<303> JOURNAL: Mucosal Immunol
<304> VOLUME: 9
<305> ISSUE: 1
<306> PAGES: 137-145
<307> DATE: 2016-01-01
<313> RELEVANT RESIDUES IN SEQ ID NO: (1)..(525)
<300> PUBLICATION INFORMATION:
<301> AUTHORS: Tian X, Zhang A, Qiu C, Wang W, Yang Y, Qiu C, Liu A,
      Zhu L, Yuan S, Hu H, Wang W, Wei Q, Zhang X and Xu J.
<302> TITLE: The upregulation of LAG-3 on T cells defines a
      subpopulation with functional exhaustion and correlates with
      disease progression in HIV-infected subjects
<303> JOURNAL: J. Immunol.
<304> VOLUME: 194
```

```
<305> ISSUE: 8
<306> PAGES: 3873-3882
<307> DATE: 2015
<313> RELEVANT RESIDUES IN SEQ ID NO: (1)..(525)
<300> PUBLICATION INFORMATION:
<301> AUTHORS: Juno,J.A., Stalker,A.T., Waruk,J.L., Oyugi,J., Kimani,M.,
      Plummer,F.A., Kimani,J. and Fowke,K.R.
<302> TITLE: Elevated expression of LAG-3, but not PD-1, is associated
      with impaired iNKT cytokine production during chronic HIV-1
      infection and treatment
<303> JOURNAL: Retrovirology
<304> VOLUME: 12
<305> ISSUE: 17
<306> PAGES: 0-0
<307> DATE: 2015
<313> RELEVANT RESIDUES IN SEQ ID NO: (1)..(525)
<300> PUBLICATION INFORMATION:
<301> AUTHORS: Huard B, Mastrangeli R, Prigent P, Bruniquel D, Donini S,
      El-Tayar N, Maigret B, Dreano M and Triebel F.
<302> TITLE: Characterization of the major histocompatibility complex
      class II binding site on LAG-3 protein
<303> JOURNAL: Proc. Natl. Acad. Sci. U.S.A.
<304> VOLUME: 94
<305> ISSUE: 11
<306> PAGES: 5744-5749
<307> DATE: 1997
<313> RELEVANT RESIDUES IN SEQ ID NO: (1)..(525)
<300> PUBLICATION INFORMATION:
<301> AUTHORS: Bruniquel D, Borie N and Triebel F.
<302> TITLE: Genomic organization of the human LAG-3/CD4 locus
<303> JOURNAL: Immunogenetics
<304> VOLUME: 47
<305> ISSUE: 1
<306> PAGES: 96-98
<307> DATE: 1997
<313> RELEVANT RESIDUES IN SEQ ID NO: (1)..(525)
<300> PUBLICATION INFORMATION:
<301> AUTHORS: Blum MD, Wong GT, Higgins KM, Sunshine MJ and Lacy E.
<302> TITLE: Reconstitution of the subclass-specific expression of CD4
      in thymocytes and peripheral T cells of transgenic mice:
      identification of a human CD4 enhancer
<303> JOURNAL: J. Exp. Med.
<304> VOLUME: 177
<305> ISSUE: 5
<306> PAGES: 1343-1358
<307> DATE: 1993
<313> RELEVANT RESIDUES IN SEQ ID NO: (1)..(525)
<300> PUBLICATION INFORMATION:
<301> AUTHORS: Baixeras E, Huard B, Miossec C, Jitsukawa S, Martin M,
      Hercend T, Auffray C, Triebel F and Piatier-Tonneau D.
<302> TITLE: Characterization of the lymphocyte activation gene
      3-encoded protein. A new ligand for human leukocyte antigen class
      II antigens
<303> JOURNAL: J. Exp. Med.
<304> VOLUME: 176
<305> ISSUE: 2
<306> PAGES: 327-337
<307> DATE: 1992
<313> RELEVANT RESIDUES IN SEQ ID NO: (1)..(525)
<300> PUBLICATION INFORMATION:
<301> AUTHORS: Triebel F, Jitsukawa S, Baixeras E, Roman-Roman S,
      Genevee C, Viegas-Pequignot E and Hercend T.
<302> TITLE: LAG-3, a novel lymphocyte activation gene closely related
      to CD4
<303> JOURNAL: J. Exp. Med.
<304> VOLUME: 171
<305> ISSUE: 5
<306> PAGES: 1393-1405
<307> DATE: 1990
<313> RELEVANT RESIDUES IN SEQ ID NO: (1)..(525)

<400> SEQUENCE: 2

Met Trp Glu Ala Gln Phe Leu Gly Leu Leu Phe Leu Gln Pro Leu Trp
        -20                 -15                 -10

Val Ala Pro Val Lys Pro Leu Gln Pro Gly Ala Glu Val Pro Val Val
    -5               -1   1               5                  10
```

-continued

```
Trp Ala Gln Glu Gly Ala Pro Ala Gln Leu Pro Cys Ser Pro Thr Ile
             15                  20                  25
Pro Leu Gln Asp Leu Ser Leu Leu Arg Arg Ala Gly Val Thr Trp Gln
         30                  35                  40
His Gln Pro Asp Ser Gly Pro Pro Ala Ala Pro Gly His Pro Leu
         45                  50                  55
Ala Pro Gly Pro His Pro Ala Ala Pro Ser Ser Trp Gly Pro Arg Pro
 60                  65                  70
Arg Arg Tyr Thr Val Leu Ser Val Gly Pro Gly Leu Arg Ser Gly
 75                  80                  85                  90
Arg Leu Pro Leu Gln Pro Arg Val Gln Leu Asp Glu Arg Gly Arg Gln
             95                 100                 105
Arg Gly Asp Phe Ser Leu Trp Leu Arg Pro Ala Arg Arg Ala Asp Ala
            110                 115                 120
Gly Glu Tyr Arg Ala Ala Val His Leu Arg Asp Arg Ala Leu Ser Cys
            125                 130                 135
Arg Leu Arg Leu Arg Leu Gly Gln Ala Ser Met Thr Ala Ser Pro Pro
            140                 145                 150
Gly Ser Leu Arg Ala Ser Asp Trp Val Ile Leu Asn Cys Ser Phe Ser
155                 160                 165                 170
Arg Pro Asp Arg Pro Ala Ser Val His Trp Phe Arg Asn Arg Gly Gln
            175                 180                 185
Gly Arg Val Pro Val Arg Glu Ser Pro His His Leu Ala Glu Ser
            190                 195                 200
Phe Leu Phe Leu Pro Gln Val Ser Pro Met Asp Ser Gly Pro Trp Gly
            205                 210                 215
Cys Ile Leu Thr Tyr Arg Asp Gly Phe Asn Val Ser Ile Met Tyr Asn
 220                 225                 230
Leu Thr Val Leu Gly Leu Glu Pro Pro Thr Pro Leu Thr Val Tyr Ala
235                 240                 245                 250
Gly Ala Gly Ser Arg Val Gly Leu Pro Cys Arg Leu Pro Ala Gly Val
            255                 260                 265
Gly Thr Arg Ser Phe Leu Thr Ala Lys Trp Thr Pro Gly Gly Gly
            270                 275                 280
Pro Asp Leu Leu Val Thr Gly Asp Asn Gly Asp Phe Thr Leu Arg Leu
            285                 290                 295
Glu Asp Val Ser Gln Ala Gln Ala Gly Thr Tyr Thr Cys His Ile His
            300                 305                 310
Leu Gln Glu Gln Gln Leu Asn Ala Thr Val Thr Leu Ala Ile Ile Thr
315                 320                 325                 330
Val Thr Pro Lys Ser Phe Gly Ser Pro Gly Ser Leu Gly Lys Leu Leu
            335                 340                 345
Cys Glu Val Thr Pro Val Ser Gly Gln Glu Arg Phe Val Trp Ser Ser
            350                 355                 360
Leu Asp Thr Pro Ser Gln Arg Ser Phe Ser Gly Pro Trp Leu Glu Ala
            365                 370                 375
Gln Glu Ala Gln Leu Leu Ser Gln Pro Trp Gln Cys Gln Leu Tyr Gln
            380                 385                 390
Gly Glu Arg Leu Leu Gly Ala Ala Val Tyr Phe Thr Glu Leu Ser Ser
395                 400                 405                 410
Pro Gly Ala Gln Arg Ser Gly Arg Ala Pro Gly Ala Leu Pro Ala Gly
            415                 420                 425
```

```
His Leu Leu Leu Phe Leu Ile Leu Gly Val Leu Ser Leu Leu Leu
            430             435                 440
Val Thr Gly Ala Phe Gly Phe His Leu Trp Arg Arg Gln Trp Arg Pro
        445             450             455
Arg Arg Phe Ser Ala Leu Glu Gln Gly Ile His Pro Pro Gln Ala Gln
    460             465             470
Ser Lys Ile Glu Glu Leu Glu Gln Glu Pro Glu Pro Glu Pro Glu Pro
475             480             485             490
Glu Pro Glu Pro Glu Pro Glu Pro Glu Pro Glu Gln Leu
            495             500
```